(12) United States Patent
Fouad et al.

(10) Patent No.: US 12,329,517 B2
(45) Date of Patent: Jun. 17, 2025

(54) COGNITIVE STATE VEHICLE NAVIGATION BASED ON IMAGE PROCESSING AND MODES

(71) Applicant: Affectiva, Inc., Boston, MA (US)

(72) Inventors: Maha Amr Mohamed Fouad, New Cairo (EG); Rana el Kaliouby, Milton, MA (US); Abdelrahman N. Mahmoud, Somerville, MA (US); Panu James Turcot, Pacifica, CA (US)

(73) Assignee: Affectiva, Inc., Boston, MA (US)

( * ) Notice: Subject to any disclaimer, the term of this patent is extended or adjusted under 35 U.S.C. 154(b) by 411 days.

(21) Appl. No.: 17/378,817

(22) Filed: Jul. 19, 2021

(65) Prior Publication Data

US 2021/0339759 A1    Nov. 4, 2021

Related U.S. Application Data

(63) Continuation-in-part of application No. 16/261,905, filed on Jan. 30, 2019, now Pat. No. 11,067,405,
(Continued)

(51) Int. Cl.
*G05D 1/00* (2024.01)
*A61B 5/1171* (2016.01)
(Continued)

(52) U.S. Cl.
CPC ....... *A61B 5/1176* (2013.01); *B60W 50/0098* (2013.01); *G06V 10/764* (2022.01);
(Continued)

(58) Field of Classification Search
CPC .................................................. A61B 5/1176
See application file for complete search history.

(56) References Cited

U.S. PATENT DOCUMENTS 3,034,500 A   5/1962   Backster, Jr.
3,548,806 A   12/1970  Fisher
(Continued)

FOREIGN PATENT DOCUMENTS

CN   101535079 A  *  9/2009  ........... B60K 28/066
EP   1785744 A1   *  5/2007  ........... G01S 13/931
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Redhwan K Mawari
*Assistant Examiner* — Paul W Arellano
(74) *Attorney, Agent, or Firm* — Adams Intellex, PLC

(57) ABSTRACT

Image-based analysis techniques are used for cognitive state vehicle navigation, including an autonomous or a semi-autonomous vehicle. Images including facial data of a vehicle occupant are obtained using an in-vehicle imaging device. The vehicle occupant can be an operator of or a passenger within the vehicle. A first computing device is used to analyze the images to determine occupant cognitive state data. The analysis can occur at various times along a vehicle travel route. The cognitive state data is mapped to location data along the vehicle travel route. Information about the vehicle travel route is updated based on the cognitive state data and mode data for the vehicle. The updated information is provided for vehicle control. The mode data is configurable based on a mode setting. The mode data is weighted based on additional information.

26 Claims, 18 Drawing Sheets

Related U.S. Application Data which is a continuation-in-part of application No. 15/875,644, filed on Jan. 19, 2018, now Pat. No. 10,627,817, which is a continuation-in-part of application No. 15/273,765, filed on Sep. 23, 2016, now abandoned, which is a continuation-in-part of application No. 14/796,419, filed on Jul. 10, 2015, now abandoned, which is a continuation-in-part of application No. 14/460,915, filed on Aug. 15, 2014, now abandoned, which is a continuation-in-part of application No. 13/153,745, filed on Jun. 6, 2011, now abandoned.

(60) Provisional application No. 63/083,136, filed on Sep. 25, 2020, provisional application No. 63/071,401, filed on Aug. 28, 2020, provisional application No. 62/679,825, filed on Jun. 3, 2018, provisional application No. 62/637,567, filed on Mar. 2, 2018, provisional application No. 62/625,274, filed on Feb. 1, 2018, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.
| | | |
|---|---|---|
| *B60W 50/00* | (2006.01) | |
| *G06V 10/764* | (2022.01) | |
| *G06V 20/56* | (2022.01) | |
| *G06V 20/59* | (2022.01) | |
| *G06V 40/16* | (2022.01) | |
| *G06V 40/20* | (2022.01) | |
| *G07C 5/02* | (2006.01) | |
| *G06V 10/44* | (2022.01) | |

(52) U.S. Cl.
CPC ............ *G06V 20/56* (2022.01); *G06V 20/597* (2022.01); *G06V 40/161* (2022.01); *G06V 40/176* (2022.01); *G06V 40/20* (2022.01); *G07C 5/02* (2013.01); *B60W 2420/403* (2013.01); *B60W 2420/408* (2024.01); *B60W 2540/10* (2013.01); *B60W 2540/12* (2013.01); *B60W 2540/229* (2020.02); *B60W 2540/30* (2013.01); *B60W 2554/4042* (2020.02); *B60W 2554/4043* (2020.02); *B60W 2555/20* (2020.02); *B60W 2556/10* (2020.02); *B60W 2556/45* (2020.02); *G06V 10/454* (2022.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,390,121 A * | 2/1995 | Wolfe ................ B60G 17/0185 280/124.101 |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,777,211 A * | 7/1998 | Binienda ............. F16H 57/0405 73/53.05 |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |

(56) References Cited

U.S. PATENT DOCUMENTS

| | | |
|---|---|---|
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,724,920 B1 | 4/2004 | Berenz et al. |
| 6,792,458 B1 | 9/2004 | Muret et al. |
| 6,847,376 B2 | 1/2005 | Engeldrum et al. |
| 6,927,694 B1 | 8/2005 | Smith et al. |
| 7,003,135 B2 | 2/2006 | Hsieh et al. |
| 7,013,478 B1 | 3/2006 | Hendricks et al. |
| 7,027,621 B1 | 4/2006 | Prokoski |
| 7,110,570 B1 | 9/2006 | Berenz et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,300,891 B2 | 10/2012 | Chen et al. |
| 8,369,608 B2 | 2/2013 | Gunaratne |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 8,738,523 B1 | 5/2014 | Sanchez et al. |
| 8,947,217 B2 | 2/2015 | Moussa et al. |
| 9,958,870 B1* | 5/2018 | Graybill .............. G05D 1/02 |
| 10,322,728 B1 | 6/2019 | Porikli et al. |
| 2001/0001848 A1* | 5/2001 | Oshizawa .......... G01C 21/3691 |
| | | 701/414 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0011399 A1 | 1/2006 | Brockway et al. |
| 2006/0019224 A1 | 1/2006 | Behar et al. |
| 2006/0143647 A1 | 6/2006 | Bill |
| 2006/0149428 A1 | 7/2006 | Kim et al. |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0167757 A1* | 7/2008 | Kanevsky .............. G07C 5/085 |
| | | 701/1 |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164073 A1* | 6/2009 | Mabuchi .............. B60N 2/0244 |
| | | 296/65.18 |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210218 A1* | 8/2009 | Collobert .............. G06F 40/284 |
| | | 704/9 |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0134302 A1 | 6/2010 | Ahn et al. |
| 2010/0266213 A1 | 10/2010 | Hill |
| 2010/0274847 A1 | 10/2010 | Anderson et al. |
| 2010/0324437 A1 | 12/2010 | Freeman |
| 2010/0332131 A1* | 12/2010 | Horvitz .............. G01C 21/3697 |
| | | 701/414 |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0109452 A1 | 5/2012 | Autran et al. |

(56) References Cited

U.S. PATENT DOCUMENTS

| | | |
|---|---|---|
| 2012/0150430 A1 | 6/2012 | French et al. |
| 2012/0271484 A1 | 10/2012 | Feit et al. |
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2013/0204455 A1 | 8/2013 | Chia et al. |
| 2014/0171752 A1 | 6/2014 | Park et al. |
| 2014/0172910 A1 | 6/2014 | Jung et al. |
| 2014/0218187 A1 | 8/2014 | Chun et al. |
| 2014/0276090 A1* | 9/2014 | Breed ............... A61B 5/1455 600/473 |
| 2015/0030175 A1* | 1/2015 | Roggenkamp ....... G10K 11/002 381/73.1 |
| 2015/0046046 A1* | 2/2015 | Muetzel ............... G07C 5/008 701/99 |
| 2015/0258995 A1 | 9/2015 | Essers et al. |
| 2016/0104486 A1 | 4/2016 | Penilla et al. |
| 2017/0003784 A1 | 1/2017 | Garg et al. |
| 2017/0297587 A1 | 10/2017 | Mimura et al. |
| 2018/0050696 A1 | 2/2018 | Misu et al. |
| 2018/0251122 A1 | 9/2018 | Golston et al. |
| 2019/0049965 A1 | 2/2019 | Tanriover |
| 2019/0135325 A1 | 5/2019 | Lisseman et al. |
| 2019/0176837 A1 | 6/2019 | Williams et al. |
| 2019/0225232 A1 | 7/2019 | Blau |
| 2020/0103980 A1 | 4/2020 | Katz et al. |
| 2020/0171977 A1 | 6/2020 | Jales Costa et al. |
| 2020/0223362 A1 | 7/2020 | Witte |
| 2020/0285871 A1 | 9/2020 | Tokizaki et al. |
| 2020/0130528 A1 | 10/2020 | Upmanue et al. |
| 2020/0409362 A1* | 12/2020 | Long .................. B60W 50/14 |

FOREIGN PATENT DOCUMENTS

| | | |
|---|---|---|
| JP | 08115367 | 7/1996 |
| JP | 3742702 B2 * | 2/2006 |
| KR | 10-2005-0021759 A | 3/2005 |
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.
International Search Report dated Apr. 16, 2012 for PCT/US2011/054125.
International Search Report dated May 24, 2012 for PCT/US2011/060900.
Xiaoyu Wang, An HOG-LBP human detector with partial occlusion handling, Sep. 29, 2009, IEEE 12th International Conference on Computer Vision, Kyoto, Japan.
Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.
Nicholas R. Howe and Amanda Ricketson, Improving the Boosted Correlogram, 2004, Lecture Notes in Computer Science, ISSN 0302-9743, Springer-Verlag, Germany.
Xuming He, et al., Learning and Incorporating Top-Down Cues in Image Segmentation, 2006, Lecture Notes in Computer Science, ISBN 978-3-540-33832-1, Springer-Verlag, Germany.
Ross Eaton, et al., Rapid Training of Image Classifiers through Adaptive, Multi-frame Sampling Methods, Oct. 2008, IEEE 37th Applied Imagery Pattern Recognition Workshop, Washington DC.
Verkruysse, Wim, Lars O. Svaasand, and J. Stuart Nelson. "Remote plethysmographic imaging using ambient light." Optics express 16.26 (2008): 21434-21445.
Albiol, Alberto, et al. "Face recognition using HOG-EBGM." Pattern Recognition Letters 29.10 (2008): 1537-1543.
Fasel, B. (Aug. 2002). Robust face analysis using convolutional neural networks. In Object recognition supported by user interaction for service robots (vol. 2, pp. 40-43). IEEE.
Matsugu, M., Mori, K., Mitari, Y., & Kaneda, Y. (2003). Subject independent facial expression recognition with robust face detection using a convolutional neural network. Neural Networks, 16(5-6), 555-559.

* cited by examiner

COGNITIVE STATE VEHICLE NAVIGATION BASED ON IMAGE PROCESSING AND MODES

RELATED APPLICATIONS

This application claims the benefit of U.S. provisional patent applications "Neural Network Synthesis Architecture Using Encoder-Decoder Models" Ser. No. 63/071,401, filed Aug. 28, 2020, and "Neural Network Training with Bias Mitigation" Ser. No. 63/083,136, filed Sep. 25, 2020.

This application is also a continuation-in-part of U.S. patent application "Cognitive State Vehicle Navigation Based on Image Processing" Ser. No. 16/261,905, filed Jan. 30, 2019, which claims the benefit of U.S. provisional patent applications "Cognitive State Vehicle Navigation Based on Image Processing" Ser. No. 62/625,274, filed Feb. 1, 2018, "Cognitive State Based Vehicle Manipulation Using Near Infrared Image Processing" Ser. No. 62/637,567, filed Mar. 2, 2018, and "Vehicle Manipulation Using Cognitive State" Ser. No. 62/679,825, filed Jun. 3, 2018.

The U.S. patent application "Cognitive State Vehicle Navigation Based on Image Processing" Ser. No. 16/261,905, filed Jan. 30, 2019 is also a continuation-in-part of U.S. patent application "Vehicle Manipulation using Occupant Image Analysis" Ser. No. 15/875,644, filed Jan. 19, 2018, which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, and "Directed Control Transfer for Autonomous Vehicles" Ser. No. 62/611,780, filed Dec. 29, 2017.

The U.S. patent application "Vehicle Manipulation using Occupant Image Analysis" Ser. No. 15/875,644, filed Jan. 19, 2018 is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The U.S. patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF INVENTION

This application relates generally to vehicle navigation and more particularly to cognitive state vehicle navigation based on image processing and modes.

BACKGROUND

Transportation routinely presents travelers with situations that can be very challenging. The situations include being stuck in gridlocked traffic, waiting in security check lines that appear never to move, among many others. Individuals travel for many reasons. The individuals travel from one location to another for financial reasons such as commuting to and from work or school; for personal reasons such as vacation, recovery, relaxation, or adventure; or for exercise, to name only a few. To the negative, the individuals who travel may be unwilling travelers, such as those people who are fleeing war, famine, natural disasters, or economic displacement. The travelers choose a mode of transportation for their travel. The choices most often are premised on convenience, availability, or cost. Transportation modes further depend on the purpose of the travel such as getting across town or hauling goods. The modes of transportation from which a traveler chooses include ground transportation, water transportation, and air transportation. Space transportation may also be available soon.

Many individuals spend substantial and consequential amounts of time getting to, waiting for, and traveling in vehicles. The individuals use public transportation networks, such as buses, trains, and airplanes; ride-sharing services such as Uber™ and Lyft™; personal vehicles; and car sharing services such as Zipcar™; to travel among various destinations. Travel times include daily commutes to and from the office, taking the kids to school, soccer practice, and piano lessons, taking the pets to the veterinary, shopping, running errands, traveling for business or vacation, and the many other common activities that require transportation. Individuals meet their transportation needs by using a variety of vehicles. The choice of vehicles available typically depends on where people live. The vehicles can range from cars and motorcycles, to buses, trains, and subways, to ride and ride sharing services, and even to unmotorized vehicles such as bicycles, skateboards, or scooters. Traveling is time consuming at its best, and loathsome, frustrating, irritating, and stressful at its worst. Rush hour traffic or accidents; inexperienced, incompetent, impaired, or dangerous vehicle operators; and poorly maintained roads, further complicate vehicular transportation. The difficulties of transportation are further compounded by operating an unfamiliar vehicle, driving in an unfamiliar city, navigating an unfamiliar public transportation network, and even by having to remember to drive on the opposite side of the road. These transportation challenges can have catastrophic consequences. Irritated operators of vehicles can experience road rage and other antisocial behaviors, while bored, sleepy, tired, impaired, distracted, or inattentive drivers can cause vehicular accidents and injury to themselves, pedestrians, bicyclists, animals, and property.

Transportation generally, and urban transportation specifically, present very difficult design, financial, and management problems that can directly impact travelers. Heavily congested surface roads and highways, and deplorably insufficient parking, each directly influence the cognitive or mental states, moods, and emotions of travelers. The congested roadways cause significantly longer and more dangerous commutes, while the lack of available parking increases the amount of time wasted looking for a place to leave a vehicle. Public transportation, if even available to the traveler at her location, presents challenges of its own, such as overfilled buses, trains, and subways during commuting hours, and underused routes due to lack of interest, poor planning, and other factors. The increased use of bicycles through bicycle-sharing services presents its own further challenges. Challenging or dangerous situations arise when vehicles and bicycles share overfilled roadways that were not originally designed for multi-use scenarios. While vehicle operators and passengers may not be directly involved in the management and financing of transportation systems, those operators directly experience and suffer from the frustration and annoyance of using the transportation systems, all while carrying the tax burden of paying to build, operate, maintain, and upgrade those systems.

SUMMARY

Image-based analysis techniques are used for cognitive state vehicle navigation, including an autonomous or a semi-autonomous vehicle. Images including facial data of a vehicle occupant are obtained using an in-vehicle imaging device. The vehicle occupant can be an operator of or a passenger within the vehicle. A first computing device is used to analyze the images to determine occupant cognitive state data. The analysis can occur at various times along a vehicle travel route. The cognitive state data is mapped to location data along the vehicle travel route. Information about the vehicle travel route is updated based on the cognitive state data and mode data for the vehicle. The updated information is provided for vehicle control. The mode data is configurable based on a mode setting. The mode data is weighted based on additional information.

In disclosed techniques, cognitive state vehicular navigation uses occupant image-based analysis and modes. The vehicle to be manipulated can be an autonomous vehicle, a semi-autonomous vehicle, and so on. An in-vehicle imaging device such as a camera is used to collect cognitive state data from an occupant of the vehicle. The occupant can be the operator of the vehicle, a backup operator, or a passenger in the vehicle. The cognitive state data can include image data, facial data, etc. Other in-vehicle sensors can include a microphone for collecting voice data or audio data, and sensors to collect physiological data. Data relating to the vehicle can also be collected. Additional sensors can be used to collect data outside the vehicle, including image sensors, radar sensors, weather sensors, light sensors, and so on. The cognitive state data is collected from the operator or passenger of a vehicle. The vehicle can be a first vehicle, a second vehicle, a public transportation vehicle, a shared transportation vehicle, etc. The image data and facial image data can be captured using one or more cameras or another image capture apparatus. One or more cognitive state profiles are learned for the occupant of the vehicle. The one or more cognitive state profiles are based on the cognitive state data that was obtained. The cognitive state profile can include cognitive states, mental states, emotional states, moods, preferences of the occupant such as vehicle preferences, vehicle operating preferences, and so on. Further cognitive state data is captured from the occupant. The further cognitive state data can be collected while the occupant is in a second vehicle. The second vehicle can be the same vehicle, a second vehicle, a vehicle from a fleet of vehicles, and the like. The further cognitive state data is compared with the cognitive state profile that was generated for the occupant. The comparing of the further cognitive state data can include identifying the occupant of the second vehicle, determining any differences in cognitive state data collected within the vehicle with that cognitive state data collected within the second vehicle, and so on. The second vehicle is manipulated based on the comparing of the further cognitive state data. The manipulation of the second vehicle can be the same as the manipulation of a first vehicle, can be adapted to a specific make or class of the second vehicle, can be tailored to the second vehicle based on tires or other equipment, can be modified based on weather patterns, traffic patterns, and so on.

A computer-implemented method for vehicle navigation is disclosed comprising: obtaining one or more images of a vehicle occupant using a first imaging device within a vehicle, wherein the one or more images include facial data of the vehicle occupant; analyzing, using a first computing device, the one or more images to determine cognitive state data for the vehicle occupant; mapping the cognitive state data to location data along a vehicle travel route; updating information about the vehicle travel route based on the cognitive state data and mode data for the vehicle; and providing the information that was updated for vehicle control. In some embodiments, the method includes obtaining audio information from the occupant of the vehicle and augmenting the analyzing based on the audio information. The occupant can be a driver or operator of the vehicle or can be a passenger within the vehicle. The vehicle can be an autonomous vehicle or a semi-autonomous vehicle. The mode data can be configurable based on a mode setting. The mode setting can include a driving style. The driving style can include fastest route mode data. The driving style can include an acceleration and/or braking profile. The mode setting can include a comfort mode. The comfort mode can include an anti-motion sickness mode. Some embodiments further comprise weighting the mode data. The weighting the mode data can be based on the vehicle travel route. The mode data can be weighted based on information about one or more vehicle occupants. The mode data can be weighted based on crowdsourced travel route information.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
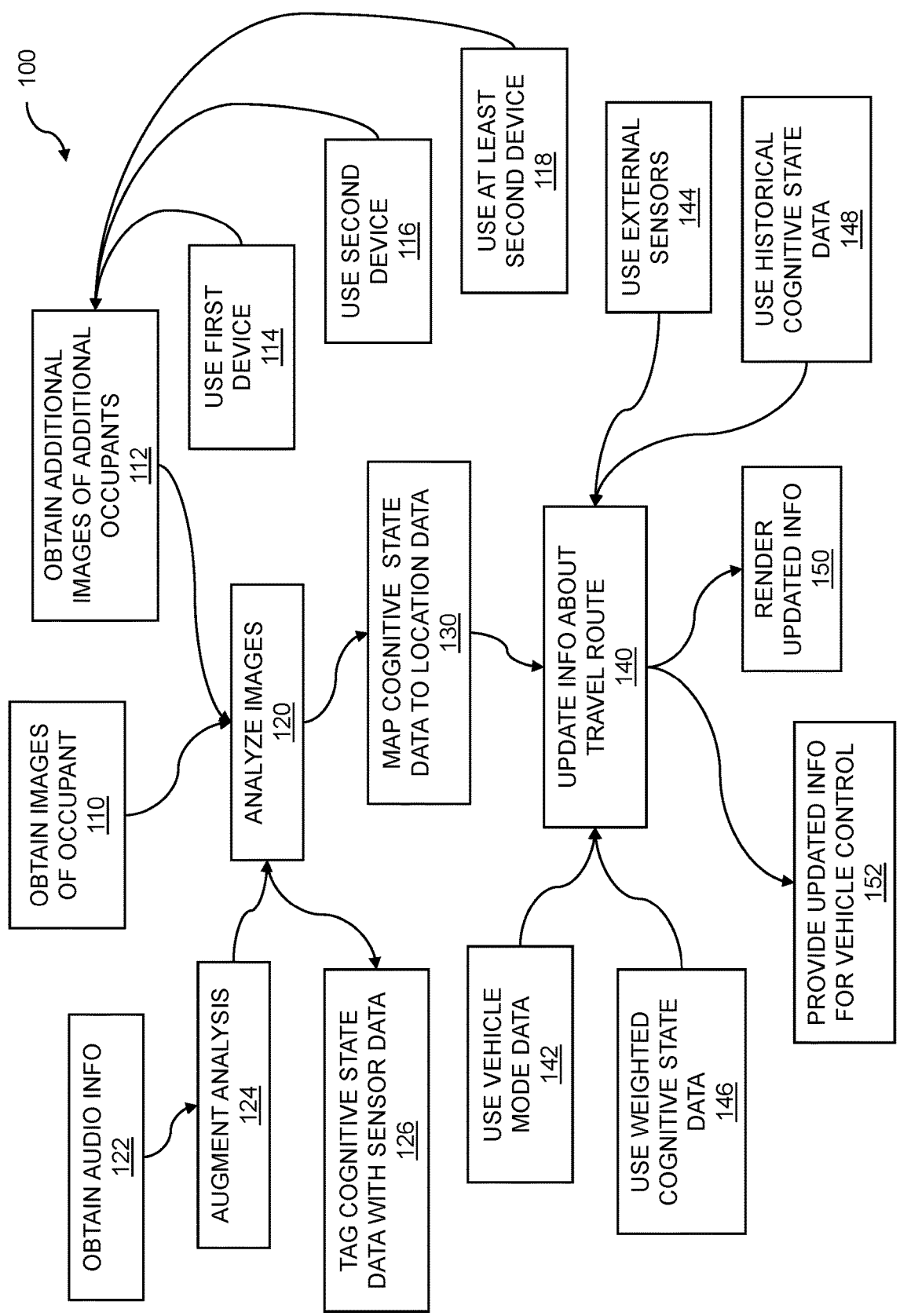
FIG. 1 is a flow diagram for cognitive state vehicle navigation.

Many individuals spend hundreds of hours or more per year traveling in vehicles. The vehicles that are typically used for travel include buses, trains, airplanes, automobiles, ride share vehicles, and so on. The hours that individuals spend in vehicles are spent commuting, running errands, meeting appointments, traveling, etc. An individual who is traveling within or atop a vehicle can experience a wide range of cognitive states. The individual's cognitive states can be determined by analyzing cognitive state data that can be collected from the individual. The cognitive state data can include image data, facial data, audio data, voice data, speech data, non-speech vocalizations, physiological data, etc. The analysis of the cognitive state data for the vehicle occupant can be used to determine a vehicle travel route best suited to the cognitive state of the vehicle occupant. That is, if the vehicle occupant is feeling stress, then a travel route can be suggested which is ranked as "low stress". The travel route can be ranked based on a range of factors such as crowd-sourced evaluation, directness of the travel route, amount of traffic, incidents of accidents free travel, presence of construction, and so on. Similarly, if the vehicle occupant is feeling happy, then a travel route that is scenic or otherwise ranked as "happy" can be recommended.

Other determinations can be made based on the vehicle occupant's cognitive state. The determinations can include whether the occupant should operate the vehicle, should take a break from traveling in the vehicle, should seek an alternative travel route, etc. The determinations and travel route recommendations have the direct benefits of road safety improvement, transportation experience enhancement, etc. Further, collecting cognitive state data enables adaptation of vehicle operating characteristics and vehicle environmental experiences for the operators and passengers. The vehicle in which the vehicle occupant or occupants are traveling can be an autonomous vehicle, a semi-autonomous vehicle, etc. The benefits of manipulating an autonomous vehicle or a semi-autonomous vehicle range from reducing the time required to configure a vehicle to an individual to verifying that the individual is in a cognitive state capable of operating the vehicle, is permitted to operate the vehicle, etc. The enhanced transportation experience for the individual includes autonomous operation, security, or comfort. The road safety improvements derive from aiding the individual who is navigating in foreign surroundings or operating an unfamiliar vehicle, and from preventing a sleepy, impaired, or inattentive individual from operating the vehicle.

In addition to the cognitive state that is mapped to location data along a vehicle travel route, mode data for the vehicle is used to modify, augment, change, influence, etc. the updating information process. Both the mode data and the cognitive state data can be weighted, either individually or in combination, to affect the updating information. Multiple modes for the vehicle can be weighted to provide an overall vehicle mode. For example, one vehicle occupant may want to get to the destination quickly, using winding and curvy back roads, while another vehicle occupant may be prone to motion sickness and may want a gentle route to be taken to prevent discomfort and nausea. Through weighting and configurability, modes can influence an appropriate vehicle travel route for occupants within the vehicle.

In the disclosed techniques, cognitive state vehicle navigation, where the vehicles can include semi-autonomous vehicles or autonomous vehicles, is based on image processing. Vehicle navigation can be performed for a variety of purposes including assisting an occupant of the vehicle, choosing routes for the vehicle, improving comfort of the occupant, reducing stress and other negative cognitive states, and so on. The vehicle navigation uses image-based analysis. One or more images of a vehicle occupant are obtained using a first imaging device within a vehicle, where the one or more images include facial data of the vehicle occupant. The first imaging device can include a camera, where the camera can include a video camera, a still camera, a camera array, a plenoptic camera, a web-enabled camera, and so on. A first computing device is used to analyze the one or more images to determine cognitive state data for the vehicle occupant. The first computing device can include an on-board computer, an electronic device used by the vehicle occupant, a server located beyond the vehicle, etc. The cognitive state data can include cognitive states, where the cognitive states can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state data is mapped to location data along a vehicle travel route. The vehicle travel route can include one or more segments. Modes can be assigned to the one or more segments of the vehicle travel route or to the entire route. Information about the vehicle travel route is updated based on the cognitive state data and mode data for the vehicle. The information that was updated can be rendered on a second computing device. The second device can include an in-vehicle device, a vehicle occupant device, a fleet monitoring computer, etc. The information that was updated can include road ratings for one or more segments of the vehicle travel route. The road ratings can comprise a route aggressiveness metric, that is, a figure of merit for how other drivers are interacting with and driving over a particular vehicle travel route. The aggressiveness metric and other route information, such as cognitive state data for occupants of other vehicles traveling along the route can be crowdsourced.

FIG. 1 is a flow diagram for cognitive state vehicle navigation. The cognitive state vehicle navigation is based on image processing and modes. One or more images of a vehicle occupant are obtained using a first imaging device within a vehicle. The one or more images can include facial data. A first computing device analyzes the one or more images to determine cognitive state data for the vehicle occupant. The cognitive state data is mapped to location data along a vehicle travel route. Information about the vehicle travel route is updated based on the cognitive state data and mode data for the vehicle. The information that was updated is provided for vehicle control. In some embodiments, vehicle navigation can simply include monitoring an occupant or driver within a vehicle. The flow 100 includes obtaining one or more images of a vehicle occupant 110 using a first imaging device within a vehicle, wherein the one or more images include facial data of the vehicle occupant. The first imaging device can include any of a variety of cameras or other image capture devices suitable for image-based analysis. A camera can include a webcam, a video camera, a still camera, a thermal imager, a CCD device, a phone camera, a three-dimensional camera, a depth camera, a light field camera, a near infrared (NIR) camera, multiple webcams used to show different views of a person, or any image capture device. In some embodiments, audio is collected in place of or in addition to images to augment the cognitive state data contained therein. In embodiments, the vehicle occupant can be the driver of the vehicle, the operator of the vehicle, a passenger of the vehicle, etc. The vehicle can be an automobile, a bus, a van, a truck, a train, an airplane, a ship, etc. The obtaining of the cognitive state data can be continuous, intermittent, occasional, etc. In embodiments, the cognitive state data that was analyzed can be based on intermittent obtaining of the one or more images that include facial data.

Embodiments further include obtaining additional images of one or more additional occupants 112 of the vehicle. The additional occupants of the vehicle can be the operator of driver of the vehicle, a passenger, and the like. The additional images can include multiple views of the first occupant, multiple views of the additional occupants, and so on. Embodiments further include obtaining one or more additional images of one or more additional vehicle occupants using the first imaging device 114. Other devices such as cameras, image capture devices, etc., can be used to obtain the one or more additional images. Further embodiments include obtaining one or more additional images of the vehicle occupant using a second imaging device 116. The second imaging device can be a camera, an image capture device, and so on. The second imaging device can be the same type of imaging device as the first imaging device or an imaging device that is different from the first imaging device. The second imaging device can be used to capture images of additional vehicle occupants. Embodiments further include obtaining one or more additional images of one or more additional vehicle occupants using at least the second imaging device 118. More than two imaging devices can be used for obtaining the images of the occupants. The imaging devices can be used to collect continuous or intermittent images, multiple views of the one or more occupants of the vehicle, and so on. In some embodiments, a multitude of cameras are used to collect image data.

The flow 100 includes analyzing, using a first computing device, the one or more images 120 to determine cognitive state data for the vehicle occupant. The first computing device can include an on-board computer within the vehicle, an electronic device that can be used by the one or more vehicle occupants, and so on. In embodiments, the first computing device can include a network-connected computing device located beyond the vehicle. The cognitive state data can include mental state data, emotional state data, mood data, and the like. In embodiments, the cognitive states can be inferred, determined, calculated, etc., from the cognitive state data. The cognitive states can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Additional cognitive states can also be included. In embodiments, the analyzing can be performed using deep learning. The deep learning can be used to learn classifiers, user profiles, and so on.

The flow 100 further includes obtaining audio information 122 from the occupant of the vehicle. The audio information can include audio information collected from within the vehicle, from outside the vehicle, etc. In embodiments, the audio information includes speech. The speech information can include speech from the driver or operator of the vehicle, speech from other occupants of the vehicle, speech from individuals outside the vehicle, speech from individuals in adjacent vehicles, etc. The audio data can include vehicle cabin noise, road noise, and the like. In embodiments, the audio information includes non-speech vocalizations. The non-speech vocalizations can include sounds produced from the driver or operator of the vehicle, sounds produced by the other occupants, etc. In embodiments, the non-speech vocalizations include grunts, yelps, squeals, snoring, sighs, laughter, filled pauses, unfilled pauses, or yawns. The audio data can be analyzed for other purposes. In embodiments, the audio information is used to perform voice recognition. The analyzing of the one or more images can be used for other purposes. In embodiments, the one or more images can be used to perform facial recognition. The facial recognition can be used to identify occupants of the vehicle. The facial recognition can be used to configure the vehicle, such as adjusting seats, mirrors, climate control, entertainment selection, etc., based on facial recognition of the vehicle driver. The facial recognition can be used to lock out operation of the vehicle by an unauthorized driver, a distracted or impaired driver, etc. In embodiments, the facial recognition is used to generate vehicle seating maps.

In embodiments the flow 100 includes augmenting the analyzing 124 based on the audio information. The augmenting analysis with the audio information can be used to improve analysis, to enable analysis, and so on. In one usage example, an image of the driver of the vehicle may show the driver with their hand over her or his mouth. By augmenting the image with non-speech vocalization data that includes a yawn, cognitive states of the driver such as sleepiness, boredom, etc., can be determined. In embodiments, the augmenting the analyzing can be based on other information such as physiological information. The physiological information can include heart rate, heart rate variability, electrodermal activity, acceleration, and the like. The flow 100 further includes tagging the cognitive state data with sensor data 126. The sensor data can include state data for various controls, conditions, etc., within and beyond the vehicle. In embodiments, the sensor data can include one or more of vehicle temperature, outside temperature, time of day, level of daylight, weather conditions, headlight activation, windshield wiper activation, entertainment center selection, or entertainment center volume.

The flow 100 includes mapping the cognitive state data to location data 130 along a vehicle travel route. The cognitive states can include cognitive state data, where the cognitive states can include drowsiness, fatigue, distraction, impairment, and so on. One or more cognitive states can be mapped to location data. In embodiments, the location data can correspond to locations along a vehicle travel route. A vehicle travel route can include one or more segments. The mapping of the cognitive state data can be based on cognitive state data collected from the driver or operator of a vehicle, from passengers in the vehicle, from occupants of other vehicles, and so on. The flow 100 includes updating information about the vehicle travel route 140 based on the cognitive state data. The updating information about the vehicle travel route is also based on vehicle mode data 142. The mode data for the vehicle can be used to modify, augment, change, influence, etc. the updating information process. Both the mode data and the cognitive state data can be weighted, either individually or in combination, to affect the updating information. Multiple modes for the vehicle can be weighted to provide an overall vehicle mode.

The flow 100 includes using external sensors 144 to augment the cognitive state data that is mapped to location data along the vehicle travel route. The cognitive state data can be augmented with data obtained from one or more sensors that sense data from outside the vehicle. The one or more sensors that sense data from outside the vehicle can include image sensors for sensing image data. The one or more sensors that sense data from outside the vehicle can include radar sensors for sensing radar data. The one or more sensors that sense data from outside the vehicle can include sensors for sensing outside temperature, time of day, level of daylight, weather conditions, traffic conditions, velocity of other vehicles, pedestrian mapping, wireless governmental travel route advisories, and so on. For example, a rainstorm during the nighttime (lack of daylight) can augment occupant cognitive state data to produce a different route recommendation or selection than might a rainstorm during broad daylight.

The updating of information about the travel route can make recommendations to occupants of vehicles, where the recommendations can include taking a break, seeking an alternative travel route, and the like. The updating information about the travel route can be based on the cognitive state data of the vehicle driver or operator, vehicle passengers, drivers or operators of other vehicles, and so on. In embodiments, the information that was updated includes road ratings for one or more segments of the vehicle travel route. The road ratings can be in reference to traffic conditions, weather conditions, road construction, etc. The ratings can be based on an aggregated cognitive state data for one or more segments of the vehicle travel route, where the aggregated cognitive state data is formed from the cognitive state data collected from a plurality of occupants of vehicles. In embodiments, the information that was updated includes an emotion metric for one or more segments of the vehicle travel route. The emotion metric can include emotions such as stress, tranquility, happiness, sadness, annoyance, etc. The vehicle travel route can be recommended based on the emotion metric.

In embodiments, the aggregated cognitive state data for one or more segments of the vehicle travel route can include a vehicle route mood map. That is, a route segment that includes a beautiful view can make the driver or passenger of a vehicle feel happy, while a route segment that includes environmental blight can make the driver or passenger feel sad or angry. The vehicle route mood map can enable vehicle route planning. In a usage example, a driver cognitive state of sadness can indicate that planning a beautiful vehicle travel route would be recommended. The route planning can include avoiding stressful areas when the vehicle occupant's cognitive state is one of stress. The route planning can include planning for other criteria or factors such as shortest route, least traffic, accident site avoidance, and the like. In embodiments, the vehicle route mood map can enable planning for routes to avoid road construction or to navigate road rearrangement, and so on. The vehicle route mood map can support other information updating. In embodiments, the vehicle route mood map can enable vehicle route redeployment. The vehicle route can be changed, updated, rerouted, redeployed, etc., based on a changed cognitive state of the vehicle driver, a traffic accident, changing weather conditions, etc.

The updating information about the vehicle travel route can be based on further criteria. The updating information can include updating for various types of vehicles. In embodiments, the aggregated cognitive state data for one or more segments of the vehicle travel route can enable autonomous vehicle control, semi-autonomous vehicle control, and so on. If aggregated cognitive state data indicates that heavy traffic is present near an accident or a construction zone, and that the plurality of vehicle occupants is stressed, then acceleration, braking, steering, and other vehicle manipulation could be transferred to autonomous control. In other embodiments, the aggregated cognitive state data for one or more segments of the vehicle travel route can enable route-based advertising placement. The route-based advertising placement could include suggestions such as activities, shops, or restaurants near high stress travel route segments, and recommendations that the driver take a break from operating the vehicle.

The flow 100 includes providing the information that was updated for vehicle control 152. The vehicle control can be accomplished by a driver within the vehicle. The vehicle can comprise an autonomous or semi-autonomous vehicle and the vehicle control can be accomplished by the vehicle. In embodiments, a rendering of the information that was updated 150 can be provided to the vehicle occupant and the vehicle control can be accomplished by the vehicle. In embodiments, the vehicle control comprises vehicle manipulation, including locking out operation; recommending a break for the occupant; recommending a different route; recommending how far to drive; responding to traffic; adjusting seats, mirrors, climate control, lighting, music, audio stimuli, or interior temperature for the second vehicle; brake activation; and steering control.

The flow 100 includes weighting the cognitive state data 146 to update travel route information, either by itself or in conjunction with the vehicle mode data. For example a particular occupant may be identified as a person who is prone to motion sickness, and therefore that person's cognitive state data may be given priority over another person's data so that the person prone to motion sickness can have a more enjoyable travel experience. The flow 100 includes using historical cognitive state data 148, either for a given route, for example, many people become nauseated when traveling along a particular winding road, or for a given occupant or occupants, for example, last week, a particular occupant became very nervous when driving at 100 mph on a western highway with no marked speed limit.

The flow 100 further includes rendering the information 150 that was updated on a second computing device. The second computing device can include a computing device within the vehicle, a computing device beyond the vehicle, a computing device used by one or more vehicle occupants, and so on. The rendering can include showing a vehicle route map on a display, where the display can include an in-dashboard display, an on-dashboard display, a heads-up display, a display on smart glasses, a display on a smart watch, and the like. The flow 100 further includes providing updated information for vehicle control 152 based on the cognitive state data and the mode data. The updates can include changing ratings of travel route segments, updating displays of cognitive mental states, and so on. The updating of the proposed vehicle route can include recommending an alternative route, presenting vehicle occupant selectable routes, etc. In embodiments, the vehicle travel route and the proposed vehicle travel route can be determined by a navigation app on the second computing device. In embodiments, the vehicle travel route is updated automatically without user intervention. In some embodiments, a route can be updated and an occupant notified of the update with a possible temporary prompt allowing the original route to be restored. In some embodiments, reasons for a route to be updated, such as the occupant becoming more stressed and the updated route being more calming, are displayed. The navigation app can be a proprietary app, a third-party app, etc. The navigation app can execute on an on-board computing device, on an electronic device used by a vehicle occupant, etc. The navigation app can include a mapping app, a GPS app, a crowd-sourced traffic information app, and so on. In embodiments, the navigation app can include Waze™, Google Maps™, Apple Maps™, Garman™, TomTom™, MapQuest™ Karta™ CoPilot GPS™, or InRoute™. In other embodiments, the mapping is performed based on GPS data for the vehicle. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
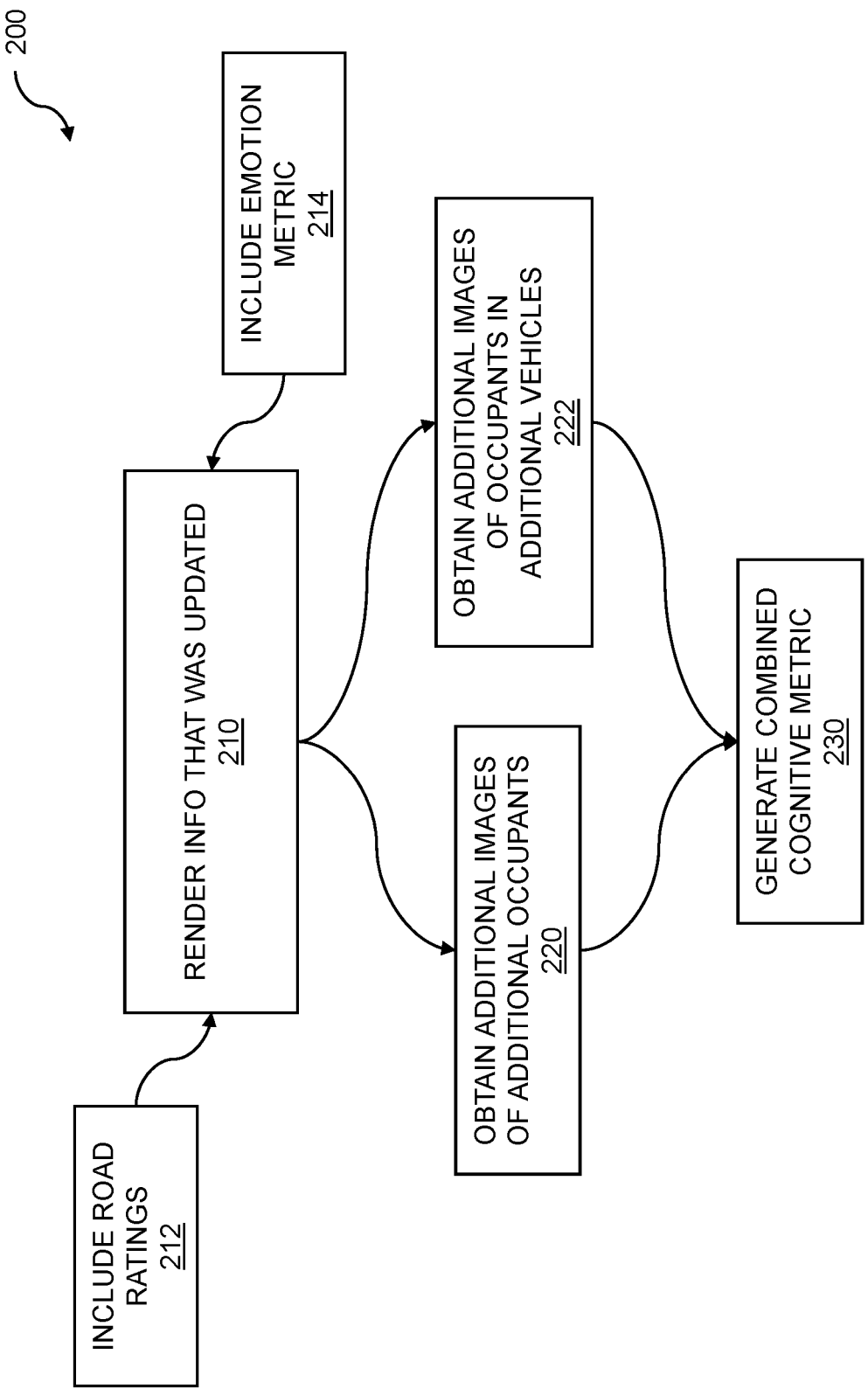
FIG. 2 is a flow diagram for vehicle route updating.

FIG. 2 is a flow diagram for vehicle route updating. The route updating includes cognitive state vehicle navigation that is based on image processing. Images of a vehicle occupant are obtained using a first imaging device within a vehicle. The images include facial data of the vehicle occupant. Other data such as audio data or physiological data can also be collected. The images are analyzed to determine cognitive state data for the vehicle occupant. The audio data or the physiological data may also be analyzed. The cognitive state data is mapped to location data along a vehicle travel route. The route can include one or more segments to which the cognitive state data can be mapped. Information about the vehicle travel route can be updated based on the cognitive state data and mode data for the vehicle.

The flow 200 includes rendering the information that was updated 210 on a second computing device. The second computing device can be coupled to the vehicle, such as an in-dashboard display, a dashboard-mounted display, a heads-up display, and so on. The second computing device can be an electronic device associated with the vehicle occupant. The second computing device can include a smartphone, a PDA, a tablet, a laptop computer, a wearable computer such as a smartwatch or smart glasses, and the like. In embodiments, the information that was updated can include road ratings 212 for one or more segments of the vehicle travel route. The road ratings can be based on a numerical value, a crowd-sourced rating, a computed value, and so on. The road ratings can be rendered as a score, a color, an emoji, a symbol, etc. The road ratings can be based on using a navigation app, where the navigation app route computation can be performed by the second computing device. The second computing device can be located within the vehicle, and can include a smartphone, PDA, tablet, etc. In embodiments, the navigation app route computation can be performed by a network-connected computing device located beyond the vehicle. The computing device located beyond the vehicle can include a server, a cloud server, a mesh server, a distributed server, and the like. In embodiments, the navigation app can include Waze™, Google Maps™, or Apple Maps™. The rendering of information that was updated can also be based on other factors, parameters, thresholds, and so on. In embodiments, the information that was updated can include an emotion metric 214 for one or more segments of the vehicle travel route. An emotion metric can be used to determine one or more emotions, an intensity of an emotion, a duration of an emotion, and so on. The emotions can include happiness, sadness, anger, boredom, and so on. In embodiments, the emotion metric can be based on the analysis of the images of the vehicle occupant.

The flow 200 includes obtaining additional images of one or more additional occupants 220 of the vehicle. The additional occupants of the vehicle can include the operator of the vehicle, passengers within the vehicle, and so on. The additional images can include multiple angle views of the additional occupants of the vehicle. The additional images can be analyzed to determine one or more cognitive states of the additional vehicle occupants. In embodiments, the flow 200 includes obtaining one or more additional images of one or more additional occupants of one or more additional vehicles 222. The additional occupants can be located in vehicles that are adjacent to the first vehicle from which images of occupants were collected or in vehicles that are remote from the first vehicle. The additional occupants can have cognitive state data that is similar to or different from that of the occupant of the first vehicle. The flow 200 includes generating a combined cognitive metric 230 for the vehicle occupant and the one or more additional occupants. The combined cognitive metric can be used to determine an intensity, a duration, a decay, and so on of the cognitive states, mental states, emotional states, etc., of the occupants of the vehicle. In embodiments, the one or more additional images are used to determine aggregated cognitive state data for one or more segments of the vehicle travel route. The aggregated cognitive state data can be used to determine whether the travel route should be updated based on the aggregated cognitive state. In embodiments, the aggregated cognitive state data for one or more segments of the vehicle travel route can include a vehicle route mood map. The vehicle route mood map can be used to show whether the one or more segments of the vehicle travel route make the vehicle occupants, happy, sad, angry, stressed, etc. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
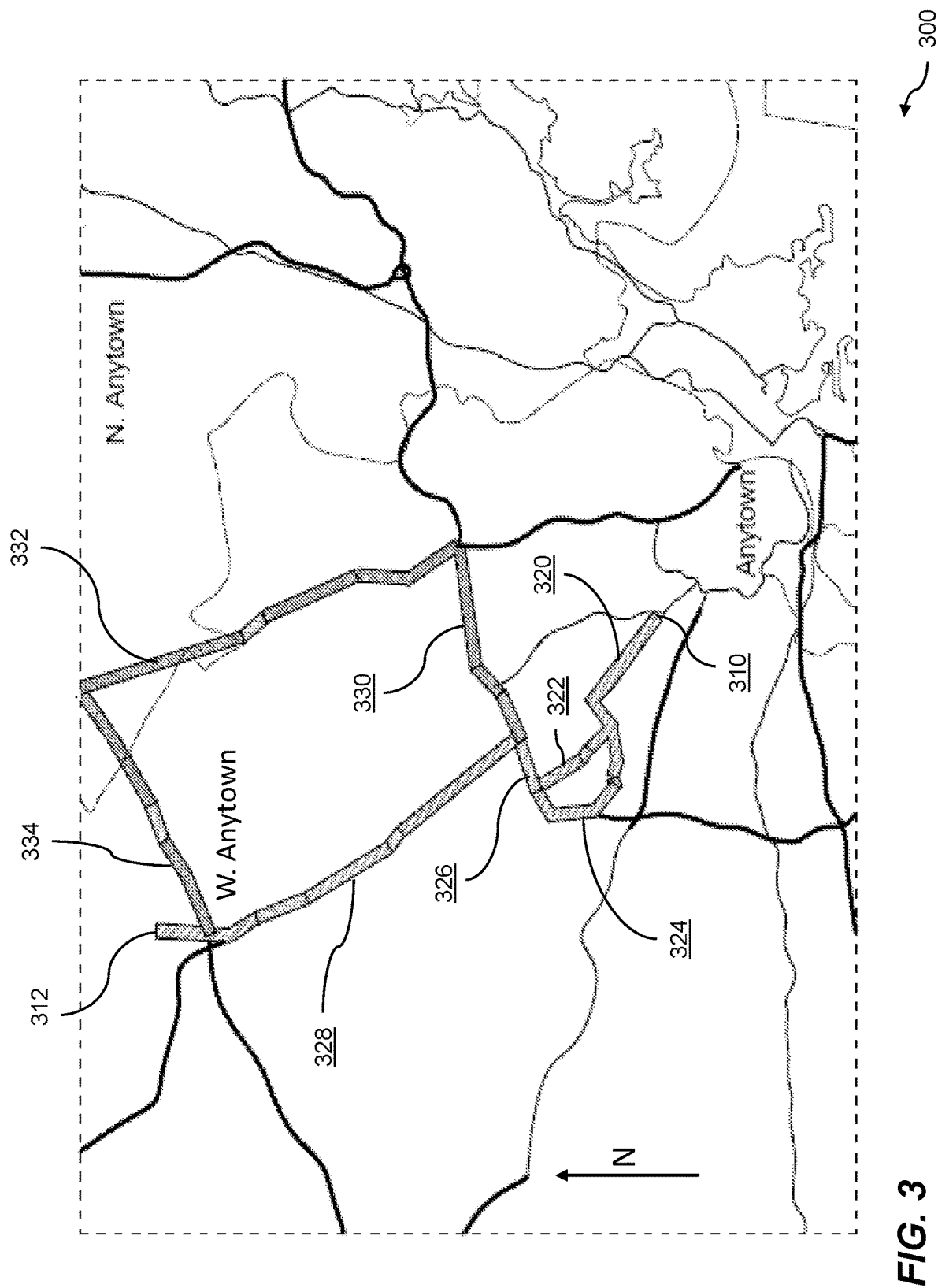
FIG. 3 shows updated travel routes based on cognitive state.

FIG. 3 shows updated travel routes 300 based on cognitive state. The one or more cognitive states of a vehicle occupant can be used to update travel routes. A plurality of travel routes can be suggested, and segments of the travel route can be rated based on the cognitive states of the vehicle occupant. Images of a vehicle occupant are obtained using a first imaging device within a vehicle, where the one or more images include facial data of the vehicle occupant. The images are analyzed to determine cognitive state data for the occupant. The cognitive state data is mapped to location data along a vehicle travel route, and information about the vehicle travel route is updated based on the cognitive state data and mode data for the vehicle. The information that was updated can include road ratings for one or more segments of the vehicle travel route. The information that was updated can be rendered and displayed to the vehicle occupant.

Example travel routes 300 based on cognitive states are shown on an example map with example cities such as Anytown, N. Anytown, and W. Anytown. A vehicle occupant wishes to travel from a starting location 310, near Anytown, to a destination location 312, near W. Anytown. A plurality of travel routes exists, where each route can be partitioned into one or more segments. The partitioning can be based on one or more cognitive states of a vehicle occupant, where the vehicle occupant can be a vehicle operator, a vehicle passenger, etc. In embodiments, the cognitive state can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

The travel routes can include first route, which comprises travel route segments 320, 322, 326, and 328; a second route, which comprises travel route segments 320, 324, 326, and 328; and a third route which comprises travel route segments 320, 322, 326, 330, 332, and 334. Based on a cognitive state such as stress, the various segments can be rated for low stress, moderate stress, high stress, etc. The ratings of segments can be based on other cognitive states. The ratings of the various segments can vary over time due to changing traffic conditions, an accident, a change in vehicle occupant cognitive state, etc. The level of stress experienced by the vehicle occupant can be based on complexity of a route, traffic conditions, weather conditions, and the like. The conditions can be determined based on analysis of sensor data. In embodiments, the sensor data can include one or more of vehicle temperature, outside temperature, time of day, level of daylight, weather conditions, headlight activation, windshield wiper activation, entertainment center selection, or entertainment center volume. The road ratings for the one or more segments of the vehicle travel route can be rendered for the vehicle occupant. In embodiments, low stress segments can be rendered in a first color such as green, in a first hash pattern, marked with a first emoji, etc.; moderate stress segments can be rendered in a second color such as yellow, with a second hash pattern, or a second emoji; and high stress segments can be rendered in a third color such as red, with a third hash pattern, with a third, warning emoji, and so on. The renderings of the travel route segments can vary over time based on changing travel route segment rankings.

Figure 4:
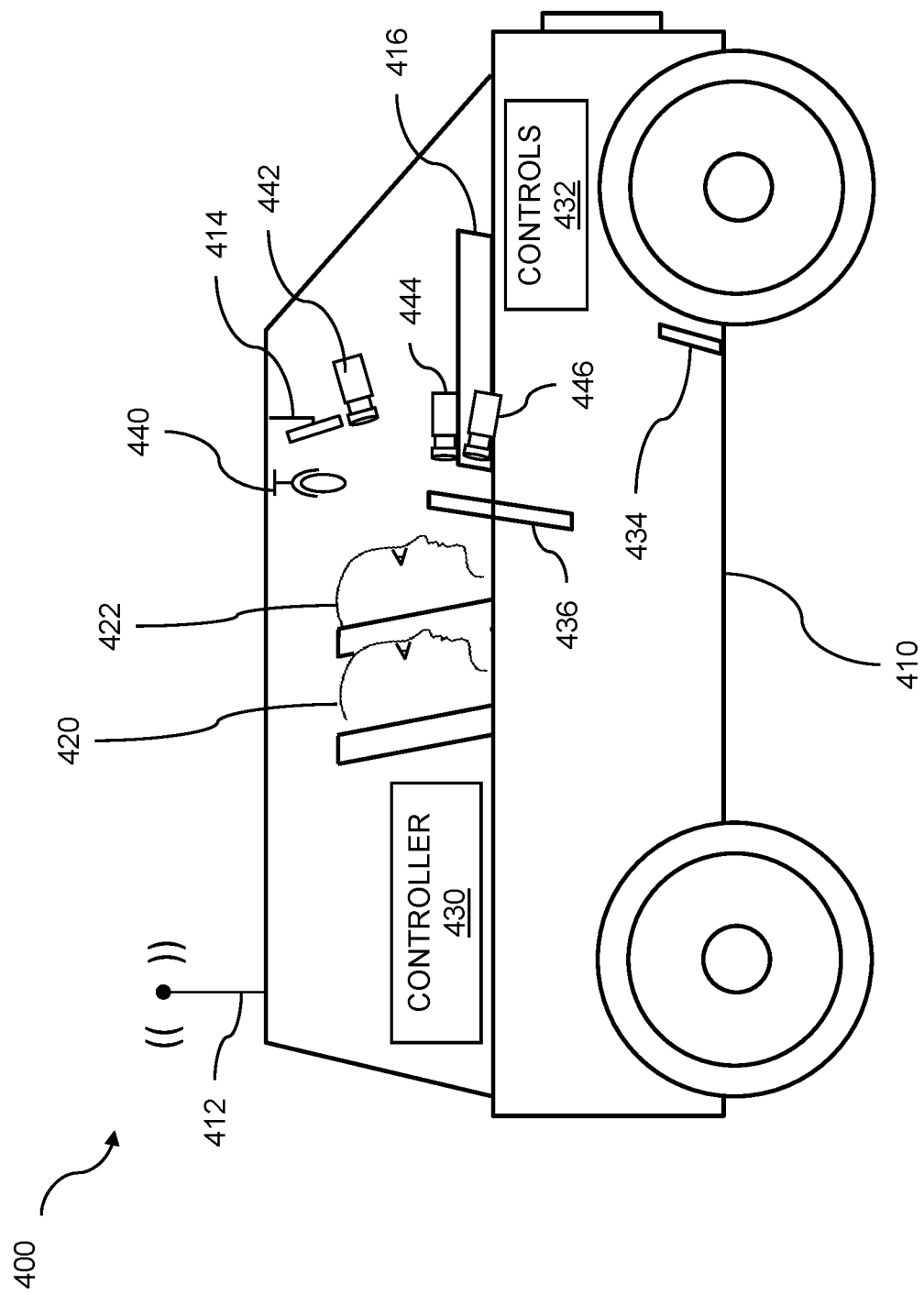
FIG. 4 is a system diagram for an interior of a vehicle.

FIG. 4 is a system diagram for an interior of a vehicle 400. Cognitive state vehicle navigation can be based on image processing. Images of a vehicle occupant are obtained using a first imaging device within a vehicle, where images include facial data. A first computing device is used to analyze the images to determine cognitive state data for the vehicle occupant. The cognitive state data is mapped to location data along a vehicle travel route, and information about the vehicle travel route is updated and provided for vehicle control, based on the cognitive state data and mode data for the vehicle. The information that was updated includes road ratings for one or more segments of the vehicle travel route. One or more occupants of a vehicle 410, such as occupants 420 and 422, can be observed using a microphone 440, one or more cameras 442, 444, or 446, and other audio and image capture techniques. The image data can include video data. The video data and the audio data can include cognitive state data, where the cognitive state data can include facial data, voice data, physiological data, and the like. The occupant can be a driver 422 of the vehicle 410, a passenger 420 within the vehicle, and so on.

The cameras or imaging devices that can be used to obtain images including facial data from the occupants of the vehicle 410 can be positioned to capture the face of the vehicle operator, the face of a vehicle passenger, multiple views of the faces of occupants of the vehicle, and so on. The cameras can be located near a rear-view mirror 414, such as camera 442, positioned near or on a dashboard 416, such as camera 444, or positioned within the dashboard, such as camera 446, and so on. The microphone or audio capture device 440 can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 410 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 410 can include standard controls such as a steering wheel 436, a throttle control (not shown), a brake 434, and so on. The interior of the vehicle can include other controls 432 such as controls for seats, mirrors, climate controls, audio systems, etc. The controls 432 of the vehicle 410 can be controlled by a controller 430. The controller 430 can control the vehicle 410 in various manners such as autonomously, semi-autonomously, assertively to a vehicle occupant 420 or 422, etc. In embodiments, the controller provides vehicle control techniques, assistance, etc. The controller 430 can receive instructions via an antenna 412 or using other wireless techniques. The controller 430 can be preprogrammed to cause the vehicle to follow a specific route. The specific route that the vehicle is programmed to follow can be based on the cognitive state of the vehicle occupant. The specific route can be chosen based on lowest stress, least traffic, best view, shortest route, and so on.

Figure 5:
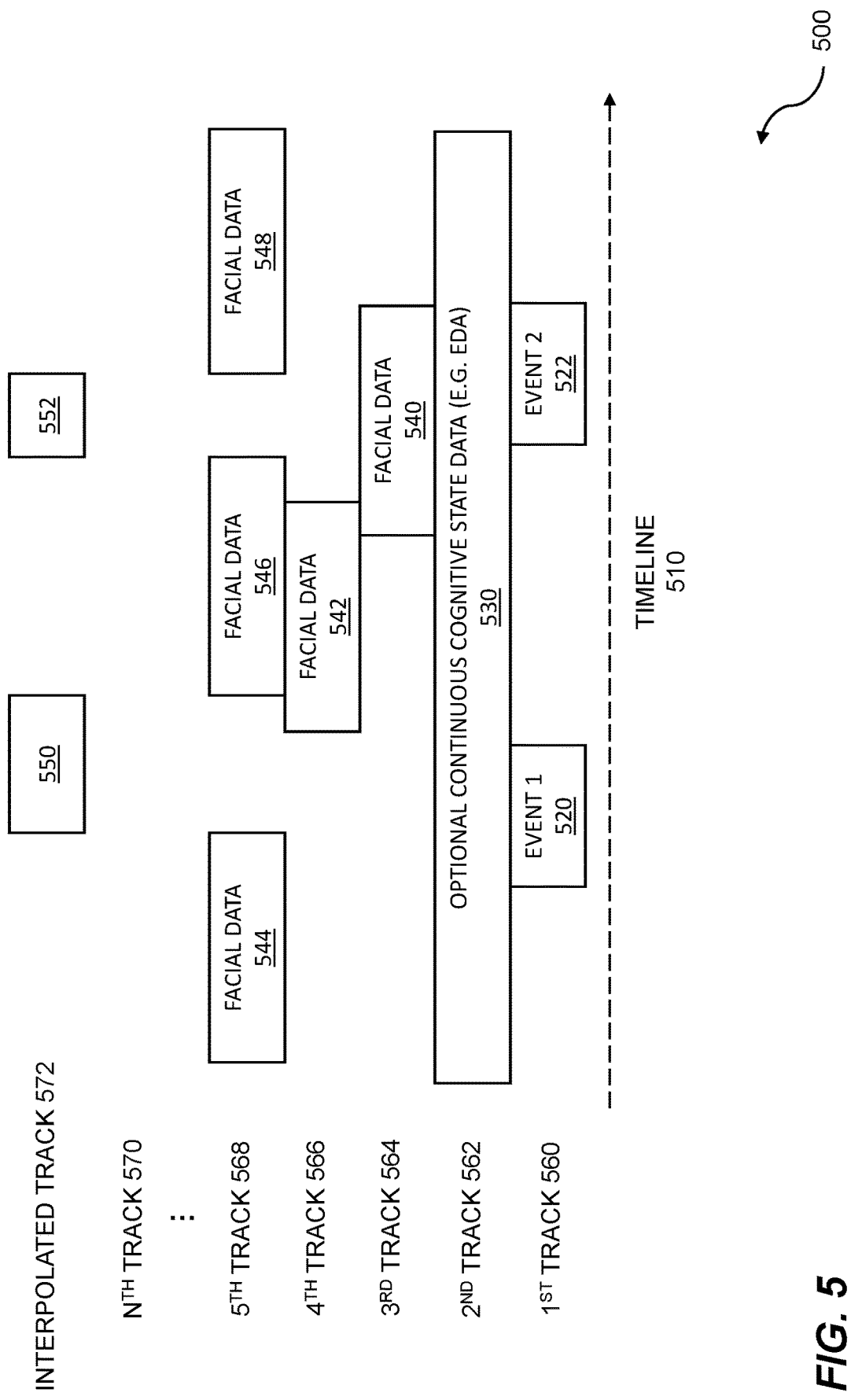
FIG. 5 is a timeline with information tracks relating to cognitive states.

FIG. 5 is a timeline with information tracks relating to cognitive states. A timeline can show one or more cognitive states that can be experienced by a vehicle occupant. The timeline can be based on vehicular cognitive data collection using multiple devices. One or more images of a vehicle occupant are obtained using a first imaging device. The one or more images are analyzed to determine cognitive state data for the vehicle occupant. The cognitive state data is mapped to location data along a vehicle travel route, and information about the vehicle travel route is updated based on the cognitive state data and mode data for the vehicle. The information that was updated is rendered and includes road ratings for one or more segments of the vehicle travel route.

The timeline 510 with information tracks 500 relates to various cognitive states. A first track 560 shows events that, in embodiments, are related to use of a computer by the individual. A first event 520 can indicate an action that the individual took (such as launching an application); an action initiated by the computer (such as the presentation of a dialog box); an external event (such as a new global positioning system (GPS) coordinate); or another event such as receiving an e-mail, a phone call, a text message, or any other type of event. In some embodiments, a photograph can be used to document an event or simply to save contextual information in the first track 560. A second event 522 can indicate another action or event in a similar manner. Such events can be used to provide contextual information and can also include information such as copies of emails, text messages, phone logs, file names, or other information that can prove useful in understanding the context of a user's actions. Thus, in embodiments, contextual information is based on one or more of a photograph, an email, a text message, a phone log, or GPS information.

A second track 562 can include continuously collected cognitive state data 530 such as electrodermal activity data. A third track 564 can include facial data. The facial data can be collected intermittently when the individual is looking toward a camera. The facial data 540 can include one or more still photographs, videos, or abstracted facial expressions which can be collected when the user looks in the direction of the camera. A fourth track 566 can include facial data that is collected either intermittently or continuously by a second camera. The facial data 542 can include one or more still photographs, videos, or abstracted facial expressions which can be collected when the user looks in the direction of that camera. A fifth track 568 can include facial data that is collected from a third camera, such as the webcam. In the example shown, the fifth track 568 includes first facial data 544, second facial data 546, and third facial data 548, which can be any type of facial data including data that can be used for determining cognitive state information. Any number of samples of facial data can be collected in any track. The cognitive state data from the various tracks can be collected simultaneously, collected on one track exclusive of other tracks, collected where cognitive state data overlaps between the tracks, and so on. When cognitive state data from multiple tracks overlap, one track's data can take precedence or the data from the multiple tracks can be combined.

Additional tracks, through the $n^{th}$ track 570, of cognitive state data of any type can be collected. The additional tracks 570 can be collected on a continuous or on an intermittent basis. The intermittent basis can be either occasional or periodic. Analysis can further comprise interpolating cognitive state data when the cognitive state data collected is intermittent, and/or imputing additional cognitive state data where the cognitive state data is missing. One or more interpolated tracks 572 can be included and can be associated with cognitive state data that is collected on an intermittent basis, such as the facial data of the fifth track 568. Interpolated data 550 and further interpolated data 552 can contain interpolations of the facial data of the fifth track 568 for the time periods where no facial data was collected in that track. Other embodiments interpolate data for periods where no track includes facial data. In other embodiments, analysis includes interpolating cognitive state analysis when the cognitive state data collected is intermittent.

The cognitive state data, such as the continuous cognitive state data 530 and/or any of the collected facial data 540, 542, 544, 546, and 548, can be tagged. The tags can include metadata related to the cognitive state data, including, but not limited to, the device that collected the cognitive state data; the individual from whom the cognitive state data was collected; the task being performed by the individual; the media being viewed by the individual; and the location, environcognitive conditions, time, date, or any other contextual information. The tags can be used to locate pertinent cognitive state data; for example, the tags can be used to retrieve the cognitive state data from a database. The tags can be included with the cognitive state data that is sent over the internet to cloud or web-based storage and/or services. As such the tags can be used locally on the machine where the cognitive state data was collected and/or remotely on a remote server or a cloud/web service.

Other tags can be related to the cognitive state data. Further embodiments can include tagging the cognitive state data with sensor data. The sensor data can be obtained from the vehicle occupant along with the obtaining of the video data or the audio data, instead of the video data or the audio data, etc. In embodiments, the sensor data can include one or more of vehicle temperature, outside temperature, time of day, level of daylight, weather conditions, headlight activation, windshield wiper activation, entertainment center selection, or entertainment center volume. Other sensor data can include physiological data related to one or more occupants of the vehicle. The physiological data can include heart rate, heart rate variability, electrodermal activity, acceleration, and the like. The tags can also be related to the cognitive state that can be determined by image-based analysis of the video, audio, or physiological data, or other techniques. In embodiments, the tags that can be applied can be based on one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 6:
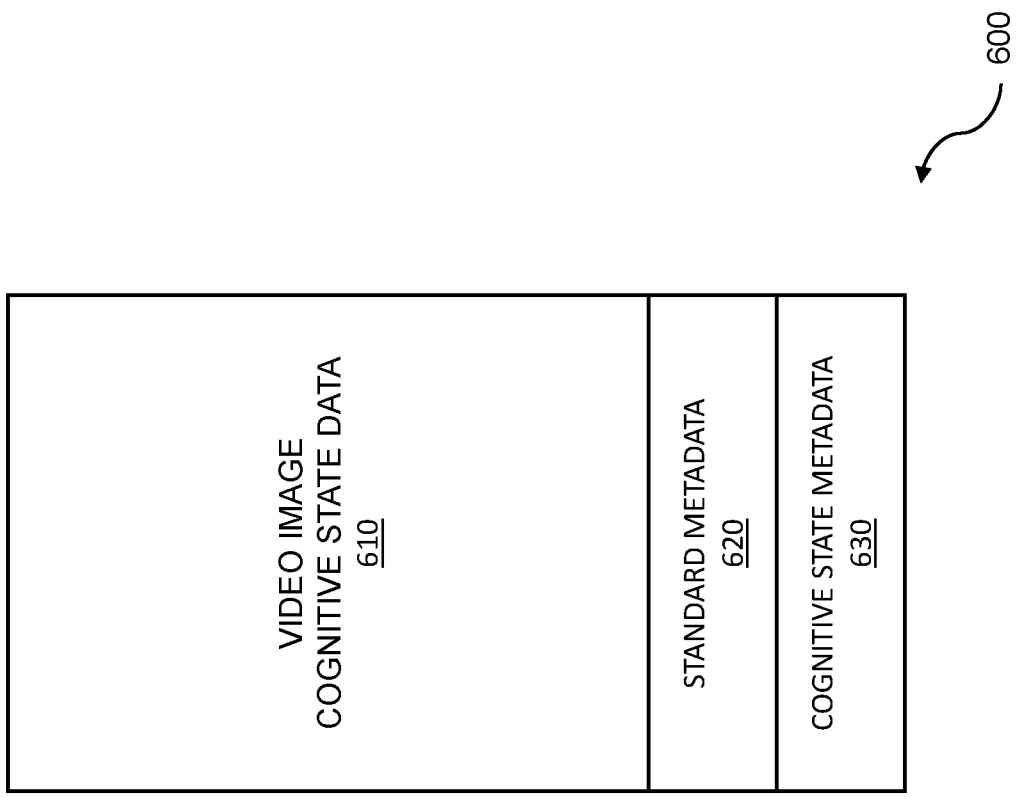
FIG. 6 shows cognitive state data with tags.

FIG. 6 shows cognitive state data with tags. Cognitive state data, including cognitive state data with tags, can be used for vehicle navigation based on image processing and modes. Images of a vehicle occupant are obtained using a first imaging device within a vehicle. The images include facial data of the vehicle occupant. The images are analyzed to determine cognitive state data for the vehicle occupant. The cognitive state data is mapped to location data along a vehicle travel route. Information about the vehicle travel route is updated based on the cognitive state data and mode data for the vehicle, where the information that was updated includes road ratings for one or more segments of the vehicle travel route. The cognitive state data, such as the cognitive state data with tags 600, includes video image cognitive state data 610 captured on an individual from a first source. In some embodiments, the source of the cognitive state data includes certain standard metadata 620 with the cognitive state data 610. For example, a video camera which includes timestamps along with video data demonstrates such metadata inclusion. A still camera which includes EXIF (or Exif) data identifying the camera model, exposure information, and day and date information in the JPEG or other image file format containing the compressed image data, shows another instance of metadata inclusion.

In embodiments, additional data which provides information about the cognitive state data 610 is determined. Such additional data can be tagged to the cognitive state data as cognitive state metadata 630. The cognitive state metadata 630 can provide information about the cognitive states useful in the analysis of the cognitive state data 610. In embodiments, the cognitive state can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state metadata 630, or additional data, is data that is not tagged to the cognitive state data by the source of the cognitive state data and not always known to the source of the cognitive state data 610. Thus, the cognitive state metadata 630 is tagged to the cognitive state data 610 by an entity that is not the original source of the cognitive state data.

In one embodiment, a video camera is used to capture the cognitive state data 610. The video camera can include standard metadata 620 such as time and date and model number of the camera, along with the video image, which in this case comprises video image cognitive state data 610, in a MPEG-4 data stream that is sent from the video camera to a cognitive state data collection machine. The standard metadata 620 can be included using standard metadata formats defined by the MPEG-4 specification. The cognitive state data collection machine can determine an identity of the individual being monitored, based on a login ID, and an activity of that individual, such as watching a particular media presentation. The cognitive state data collection machine can then tag the video image with the login ID and the name of the particular media presentation as cognitive state metadata 630. In at least one embodiment, the cognitive state data collection machine formats the cognitive state metadata as XMP metadata and includes it in the MPEG-4 file. Other embodiments determine different additional information to be used as cognitive state metadata 630 and use different formats to tag the cognitive state data 610 with the cognitive state metadata 630.

Once the data collection machine has captured cognitive state data, at least a portion of the cognitive state data tagged with the additional data is sent to a web service. The portion of the cognitive state data sent to the web service can be based on the additional contextual data collected, or can be based on cognitive state metadata 630. At the web service, portions of cognitive state data can be selected for analysis based, at least in part, on tags identifying one or more contexts. In at least one embodiment, the selected portions are based, at least in part, on identifying a particular individual. In some embodiments, the selected portions include tags identifying at least two different timestamps so that samples can be distributed over a period of time. In some embodiments, the selected portions are based, at least in part, on tags identifying a particular context. Once the portions are selected, they can be analyzed by the web service and used to create cognitive state information.

Figure 7:
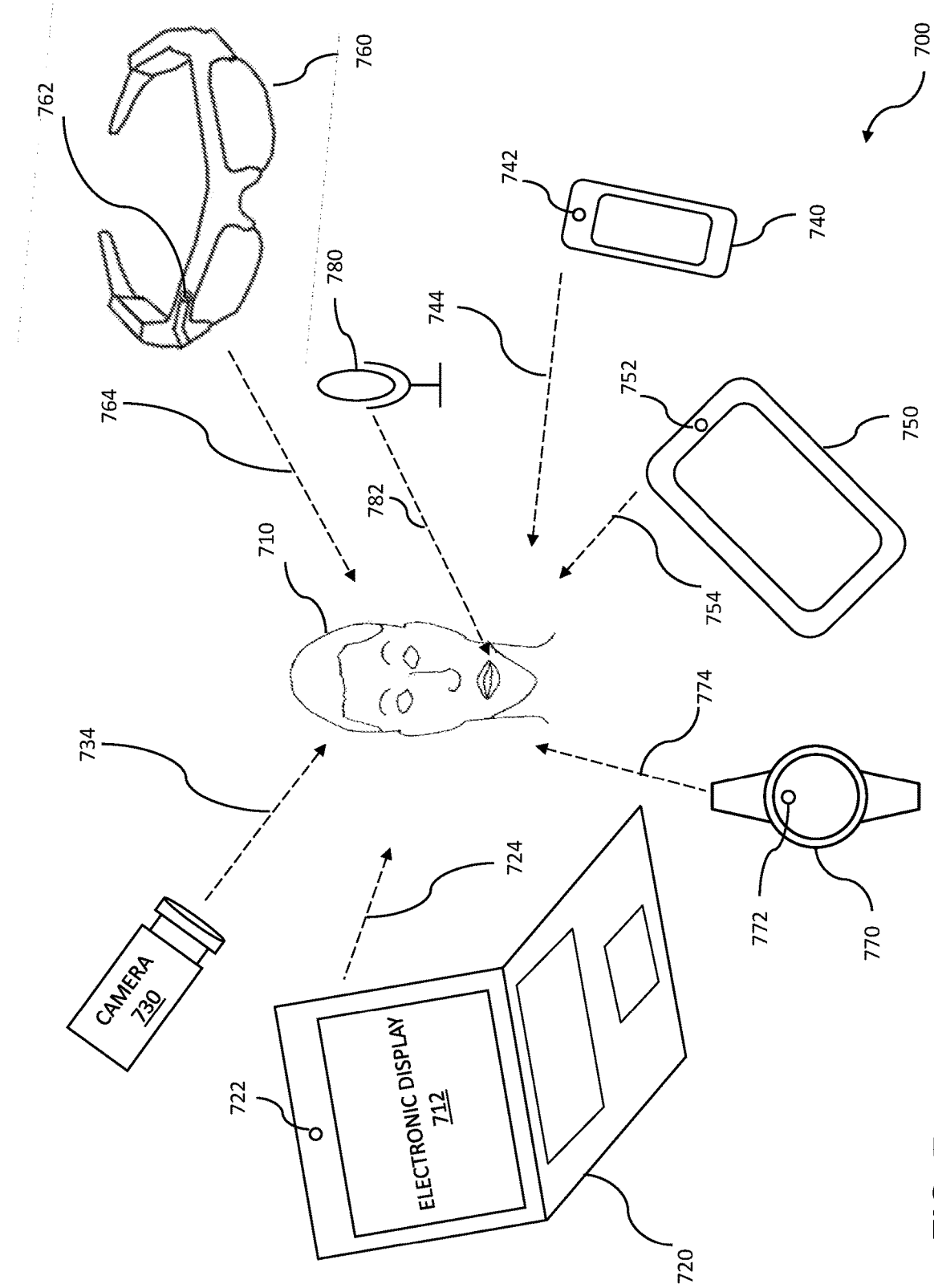
FIG. 7 shows example image and audio collection including multiple mobile devices.

FIG. 7 is a diagram showing image collection including multiple mobile devices. Cognitive state data including image data and audio data can be collected using multiple mobile devices. The collected cognitive state data can be used for cognitive state vehicle navigation based on image processing. Images including facial data are obtained from a vehicle occupant, and the images are analyzed to determine cognitive state data. The cognitive state data is mapped to location data along a vehicle travel route, and information about the vehicle travel route is updated based on the cognitive state data and mode data for the vehicle. The information that was updated can include road ratings for one or more segments of the vehicle travel route. While one person is shown, in practice the video data or audio data on any number of people can be collected. In the diagram 700, the multiple mobile devices can be used separately or in combination to collect video data, audio data, or both video data and audio data on a user 710. While one person is shown, the video data and audio data can be collected on multiple people. A user 710 can be observed as she or he is performing a task, experiencing an event, viewing a media presentation, and so on. The user 710 can be shown one or more media presentations, political presentations, social media, or another form of displayed media. The one or more media presentations can be shown to a plurality of people. The media presentations can be displayed on an electronic display 712 or another display. The data collected on the user 710 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 710 can be analyzed and viewed for a variety of purposes including expression analysis, cognitive state analysis, mental state analysis, emotional state analysis, and so on. The electronic display 712 can be on a laptop computer 720 as shown, a tablet computer 750, a cell phone 740, a television, a mobile monitor, or any other type of electronic device. In one embodiment, video data including expression data is collected on a mobile device such as a cell phone 740, a tablet computer 750, a laptop computer 720, or a watch 770. Similarly, the audio data including speech data and non-speech vocalizations can be collected on one or more of the mobile devices. Thus, the multiple sources can include at least one mobile device, such as a phone 740 or a tablet 750, or a wearable device such as a watch 770 or glasses 760. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 722, a phone camera 742, a tablet camera 752, a wearable camera 762, and a mobile camera 730. A wearable camera can comprise various camera devices, such as a watch camera 772. Sources of audio data 782 can include a microphone 780.

As the user 710 is monitored, the user might move due to the nature of the task, boredom, discomfort, distractions, or for another reason. As the user moves, the camera with a view of the user's face can be changed. Thus, as an example, if the user is looking in a first direction, the line of sight 724 from the webcam 722 is able to observe the user's face, but if the user is looking in a second direction, the line of sight 734 from the mobile camera 730 is able to observe the user's face. Furthermore, in other embodiments, if the user is looking in a third direction, the line of sight 744 from the phone camera 742 is able to observe the user's face, and if the user is looking in a fourth direction, the line of sight 754 from the tablet camera 752 is able to observe the user's face. If the user is looking in a fifth direction, the line of sight 764 from the wearable camera 762, which can be a device such as the glasses 760 shown and can be worn by another user or an observer, is able to observe the user's face. If the user is looking in a sixth direction, the line of sight 774 from the wearable watch-type device 770, with a camera 772 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 710 can also use a wearable device including a camera for gathering contextual information and/or collecting expression data on other users. Because the user 710 can move her or his head, the facial data can be collected intermittently when she or he is looking in a direction of a camera. In some cases, multiple people can be included in the view from one or more cameras, and some embodiments include filtering out faces of one or more other people to determine whether the user 710 is looking toward a camera. All or some of the expression data can be continuously or sporadically available from the various devices and other devices.

The captured video data can include facial expressions, and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 8:
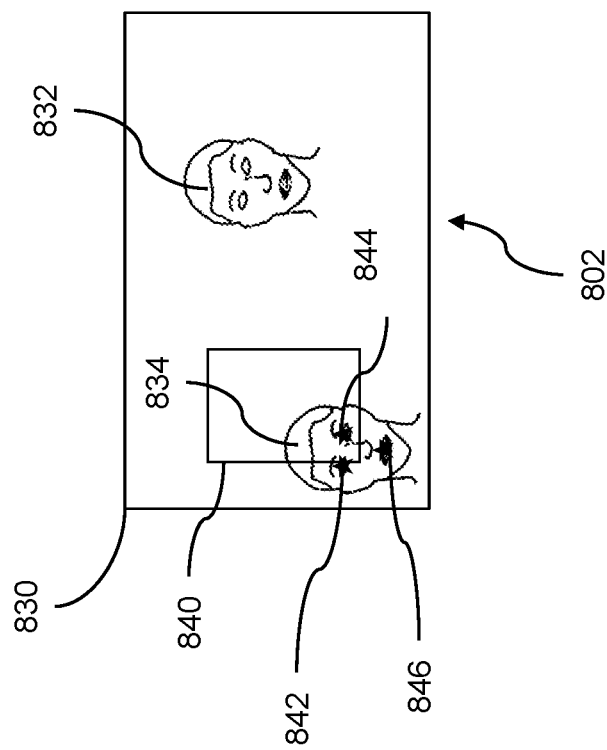
FIG. 8 illustrates feature extraction for multiple faces.
Figure 8:
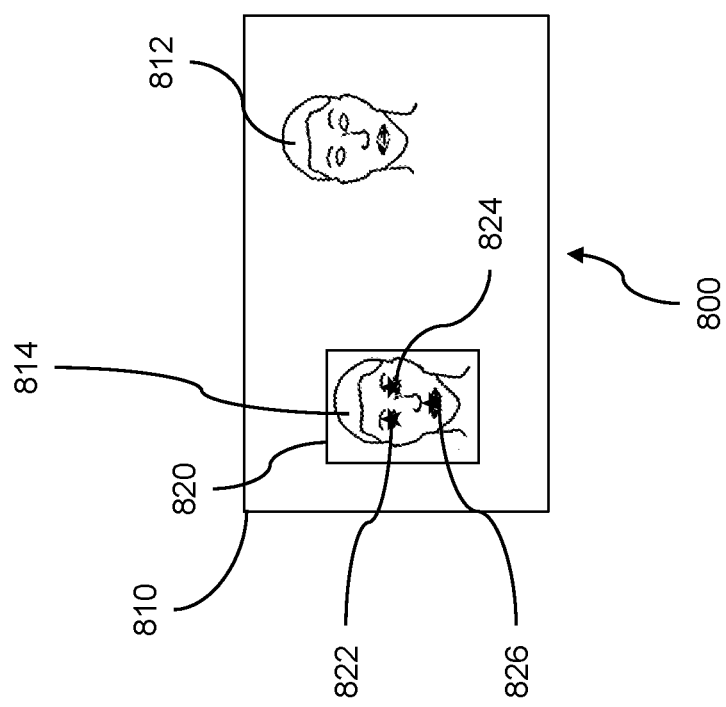

FIG. 8 illustrates feature extraction for multiple faces. Image analysis, including facial analysis, can be based on feature extraction from multiple faces. Cognitive state vehicle navigation is based on image-based analysis and mode data. Images that include facial data of a vehicle occupant are obtained using a first imaging device within a vehicle. The images are analyzed to determine cognitive state data for the vehicle occupant. The cognitive state data is mapped to location data along a vehicle travel route, and information about the vehicle travel route is updated based on the cognitive state data and mode data for the vehicle. The feature extraction for multiple faces can be performed for faces that can be detected in multiple images. In embodiments, the features of multiple faces are extracted for evaluating cognitive states. Features of a face or a plurality of faces can be extracted from collected video data. The feature extraction can be performed by analysis, by using one or more processors, by using one or more video collection devices, and by using a server. The analysis device can be used to perform face detection for a second face, as well as to perform facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or existing observation, sample, datum, etc. should be placed. The decision to place an observation into a category can be based on training the algorithm or piece of code by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When a new observation is received, then the classifier can be used to categorize the new observation. Classifiers can be used for many analysis applications, including analysis of one or more faces. The use of classifiers can be the basis of analyzing the one or more faces for gender, ethnicity, and age; of detecting the one or more faces in one or more videos; of detecting facial features and landmarks; and so on. The observations can be analyzed based on one or more of a set of quantifiable properties. The properties can be described as features and explanatory variables involving various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, etc. Algorithms for classification can be implemented using a variety of techniques, including neural networks, kernel estimation, support vector machines, use of quadratic surfaces, and so on. Classification can be used in many application areas such as computer vision, and speech and handwriting recognition. Classification can be used for biometric identification of one or more people in a single frame or in multiple frames of one or more videos.

Returning to FIG. 8, the detection of the first face, the second face, and multiple faces can include identifying facial landmarks, generating a bounding box, and predicting a bounding box and landmarks for a next frame, where the next frame can be one of a plurality of frames of a video containing faces. A first video frame 800 includes a frame boundary 810, a first face 812, and a second face 814. The video frame 800 also includes a bounding box 820. Facial landmarks can be generated for the first face 812. Face detection can be performed to initialize a second set of locations for a second set of facial landmarks for a second face within the video. Facial landmarks in the video frame 800 can include the facial landmarks 822, 824, and 826. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. The estimating of a second rough bounding box can include the bounding box 820. Bounding boxes can also be estimated for one or more other faces within the boundary 810. The bounding box can be refined, as can one or more facial landmarks. The refining of the second set of locations for the second set of facial landmarks can be based on localized information around the second set of facial landmarks. The bounding box 820 and the facial landmarks 822, 824, and 826 can be used to estimate future locations for the second set of locations for the second set of facial landmarks in a future video frame from the first video frame.

A second video frame 802 is also shown. The second video frame 802 includes a frame boundary 830, a first face 832, and a second face 834. The second video frame 802 also includes a bounding box 840 and the facial landmarks, or points, 842, 844, and 846. In other embodiments, multiple facial landmarks are generated and used for facial tracking of the two or more faces of a video frame, such as the shown second video frame 802. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to differentiate between the first face and the second face, to track either the first face, the second face, or both faces, and so on. Other facial points can correspond to the second face. As mentioned above, multiple facial points can be determined within a frame. One or more of the other facial points that are determined can correspond to a third face. The location of the bounding box 840 can be estimated, where the estimating can be based on the location of the generated bounding box 820 shown in the first video frame 800. The three facial points shown, facial points, or landmarks, 842, 844, and 846, might lie within the bounding box 840 or might not lie partially or completely within the bounding box 840. For instance, the second face 834 might have moved between the first video frame 800 and the second video frame 802. Based on the accuracy of the estimating of the bounding box 840, a new estimation can be determined for a third, future frame from the video, and so on. The evaluation can be performed, all or in part, using semiconductor-based logic.

Figure 9:
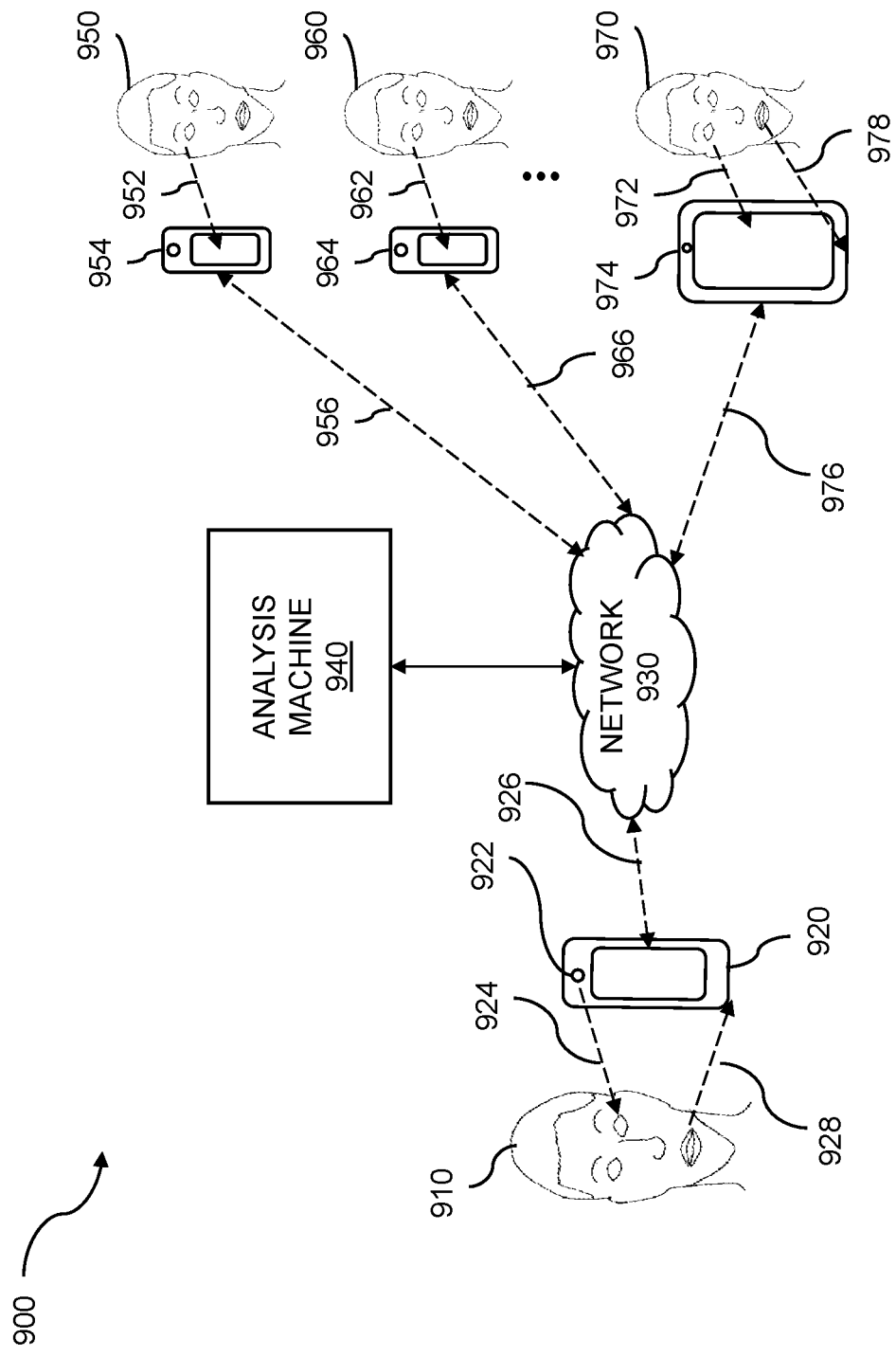
FIG. 9 shows an example of live streaming of social video and audio.

FIG. 9 shows an example of live streaming of social video and audio. The streaming of social video and social audio can be applied to cognitive state vehicle navigation based on image processing and modes. The live streaming can include cognitive state data, image data, facial data, speech data, audio data, etc. The cognitive state data can be determined by analyzing images including facial data that are obtained from a vehicle occupant. The cognitive state data is mapped to location data along a vehicle travel route, and information about the vehicle travel route is updated based on the cognitive state data and mode data for the vehicle. The updated information includes road ratings for one or more segments of the vehicle travel route. The live streaming and image analysis can be facilitated by a video capture device, a local server, a remote server, a semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams, such as webcasts, online classes, sporting events, news, computer gaming, or video conferences, can be scheduled while others can be impromptu streams that are broadcast as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen by and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 900 shows a user 910 broadcasting a video live stream and an audio live stream to one or more people as shown by a first person 950, a second person 960, and a third person 970. A portable, network-enabled, electronic device 920 can be coupled to a front-facing camera 922. The portable electronic device 920 can be a smartphone, a PDA, a tablet, a laptop computer, and so on. The camera 922 coupled to the device 920 can have a line-of-sight view 924 to the user 910 and can capture video of the user 910. The portable electronic device 920 can be coupled to a microphone (not shown). The microphone can capture voice data 928 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 940 using a network link 926 to the Internet 930. The network link can be a wireless link, a wired link, and so on. The recommendation engine 940 can recommend to the user 910 an app and/or platform that can be supported by the server and can be used to provide a video live stream, an audio live stream, or both a video live stream and an audio live stream to one or more followers of the user 910.

In the example 900, the user 910 has three followers: a first person 950, a second person 960, and a third person 970. Each follower has a line-of-sight view to a video screen on a portable, networked electronic device. In other embodiments, one or more followers follow the user 910 using any other networked electronic device, including a computer. In the example 900, a first person 950 has a line-of-sight view 952 to the video screen of a device 954; a second person 960 has a line-of-sight view 962 to the video screen of a device 964, and a third person 970 has a line-of-sight view 972 to the video screen of a device 974. The device 974 can also capture audio data 978 from the third person 970. The portable electronic devices 954, 964, and 974 can each be a smartphone, a PDA, a tablet, and so on. Each portable device can receive the video stream and the audio stream being broadcast by the user 910 through the Internet 930 using the app and/or platform that can be recommended by the recommendation engine 940. The device 954 can receive a video stream and the audio stream using the network link 956, the device 964 can receive a video stream and the audio stream using the network link 966, the device 974 can receive a video stream and the audio stream using the network link 976, and so on. The network link can be a wireless link, a wired link, a hybrid link, and so on. Depending on the app and/or platform that can be recommended by the recommendation engine 940, one or more followers, such as the followers shown 950, 960, and 970, can reply to, comment on, or otherwise provide feedback to the user 910 using their respective devices 954, 964, and 974.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers, including classifiers such as support vector machines (SVM) and random forests, perform the classification. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 10:
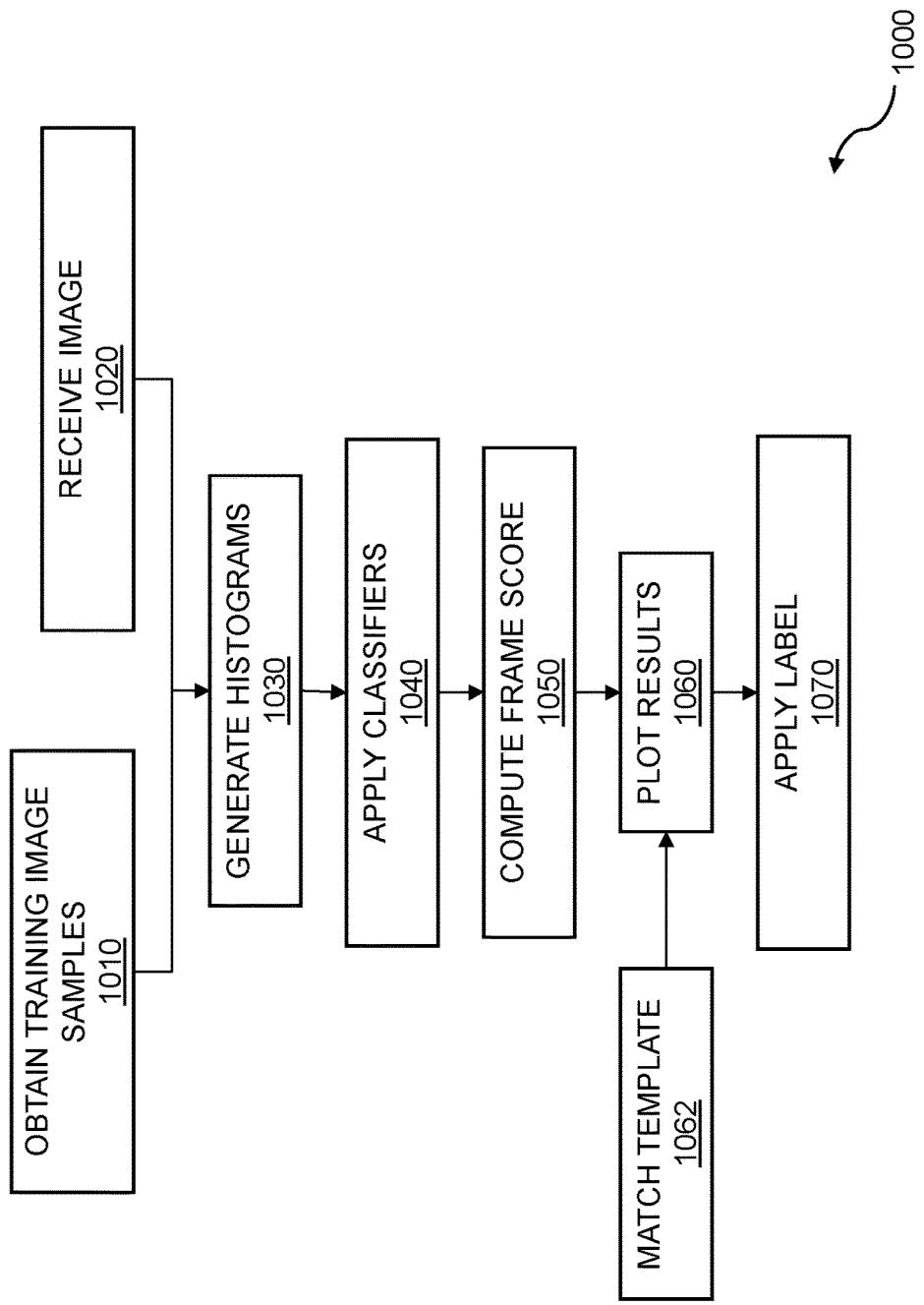
FIG. 10 is a flow diagram for detecting facial expressions.

FIG. 10 is a flow diagram for detecting facial expressions. Cognitive states can be determined by detecting and analyzing facial expressions in images. The cognitive states can be used for vehicle navigation, where the vehicle navigation can be based on image processing and modes. One or more images including facial data are obtained from a vehicle occupant by using an imaging device within a vehicle. The images are analyzed to determine cognitive state data for the vehicle occupant. The cognitive state data is mapped to location data along a vehicle travel route, and information about the vehicle travel route is updated based on the cognitive state data and mode data for the vehicle. The flow 1000, or portions thereof, can be implemented in semiconductor logic, can be accomplished using a mobile device, a server device, and so on. The flow 1000 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used separately or in combination to identify facial expressions. Based on the facial landmarks, one or more AUs can be identified by number and intensity. For example, AU12 can be used to code a lip corner puller and can be used to infer a smirk.

The flow 1000 begins by obtaining training image samples 1010. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1000 continues with receiving an image 1020. The image 1020 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1000 continues with generating histograms 1030 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1000 continues with applying classifiers 1040 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1000 continues with computing a frame score 1050. The score computed for an image, where the image can be a frame from a video, can be used to determine the presence of a facial expression in the image or video frame. The score can be based on one or more versions of the image 1020 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can identify symmetrical facial expressions (e.g. smile), asymmetrical facial expressions (e.g. outer brow raiser), and so on.

The flow 1000 continues with plotting results 1060. The results that are plotted can include one or more scores for one or more frames computed over a given time t. For example, the plotted results can include classifier probability results from analysis of HoGs for a sequence of images and video frames. The plotted results can be matched with a template 1062. The template can be temporal and can be represented by a centered box function or another function. A best fit with one or more templates can be found by computing a minimum error. Other best-fit techniques can include polynomial curve fitting, geometric curve fitting, and so on. The flow 1000 continues with applying a label 1070. The label can be used to indicate that a particular facial expression has been detected in the one or more images or video frames which constitute the image 1020 that was received. The label can be used to indicate that any of a range of facial expressions has been detected, including a smile, an asymmetric smile, a frown, and so on. Various steps in the flow 1000 may be changed in order, repeated, omitted, or the like without departing from the disclosed concepts. Various embodiments of the flow 1000 can be included in a computer program product embodied in a non-transitory computer readable medium that includes code executable by one or more processors. Various embodiments of the flow 1000, or portions thereof, can be included on a semiconductor chip and implemented in special purpose logic, programmable logic, and so on.

Figure 11:
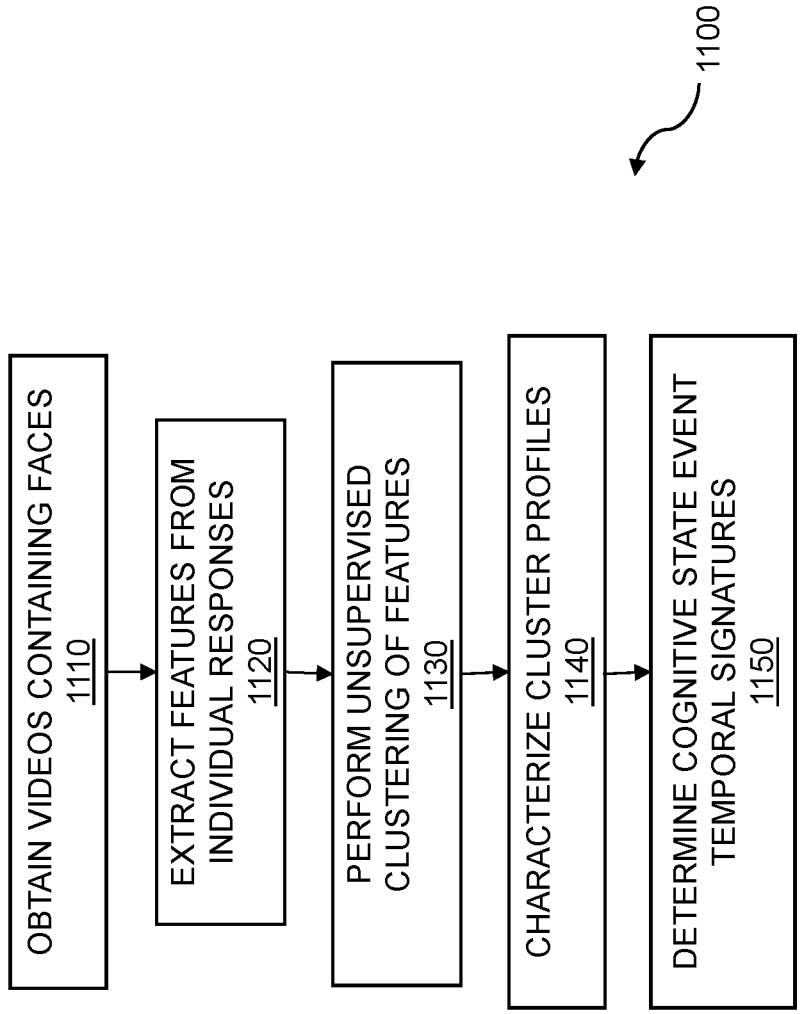
FIG. 11 is a flow diagram for the large-scale clustering of facial events.

FIG. 11 is a flow diagram for the large-scale clustering of facial events. Cognitive state vehicle navigation can be based on image-based analysis, where the analysis can use results from large-scale clustering. Images including facial data are obtained from a vehicle occupant. The images are analyzed to determine cognitive state data for the vehicle occupant. The cognitive state data is mapped to location data along a vehicle travel route. Information about the vehicle travel route is updated based on the cognitive state data, and the updated information is rendered. Cognitive state events can include facial events, speech events, etc. The large-scale clustering of facial events can be performed for data collected from a remote computing device. The facial events can be collected from people as they interact with a vehicle. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1100 includes obtaining videos containing faces 1110. The videos can be obtained using one or more cameras, where the cameras can include a webcam coupled to one or more devices employed by the one or more people using the web-based framework. The flow 1100 continues with extracting features from the individual responses 1120. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1100 continues with performing unsupervised clustering of features 1130. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1100 includes characterizing cluster profiles 1140. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared across various demographic groups, where the groups can be formed based on geographic location, age, ethnicity, gender, and so on.

The flow 1100 can include determining cognitive state event temporal signatures 1150. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1100 may be changed in order, repeated, omitted, or the like without departing from the disclosed concepts. Various embodiments of the flow 1100 can be included in a computer program product embodied in a non-transitory computer readable medium that includes code executable by one or more processors. Various embodiments of the flow 1100, or portions thereof, can be included on a semiconductor chip and implemented in special purpose logic, programmable logic, and so on.

Figure 12:
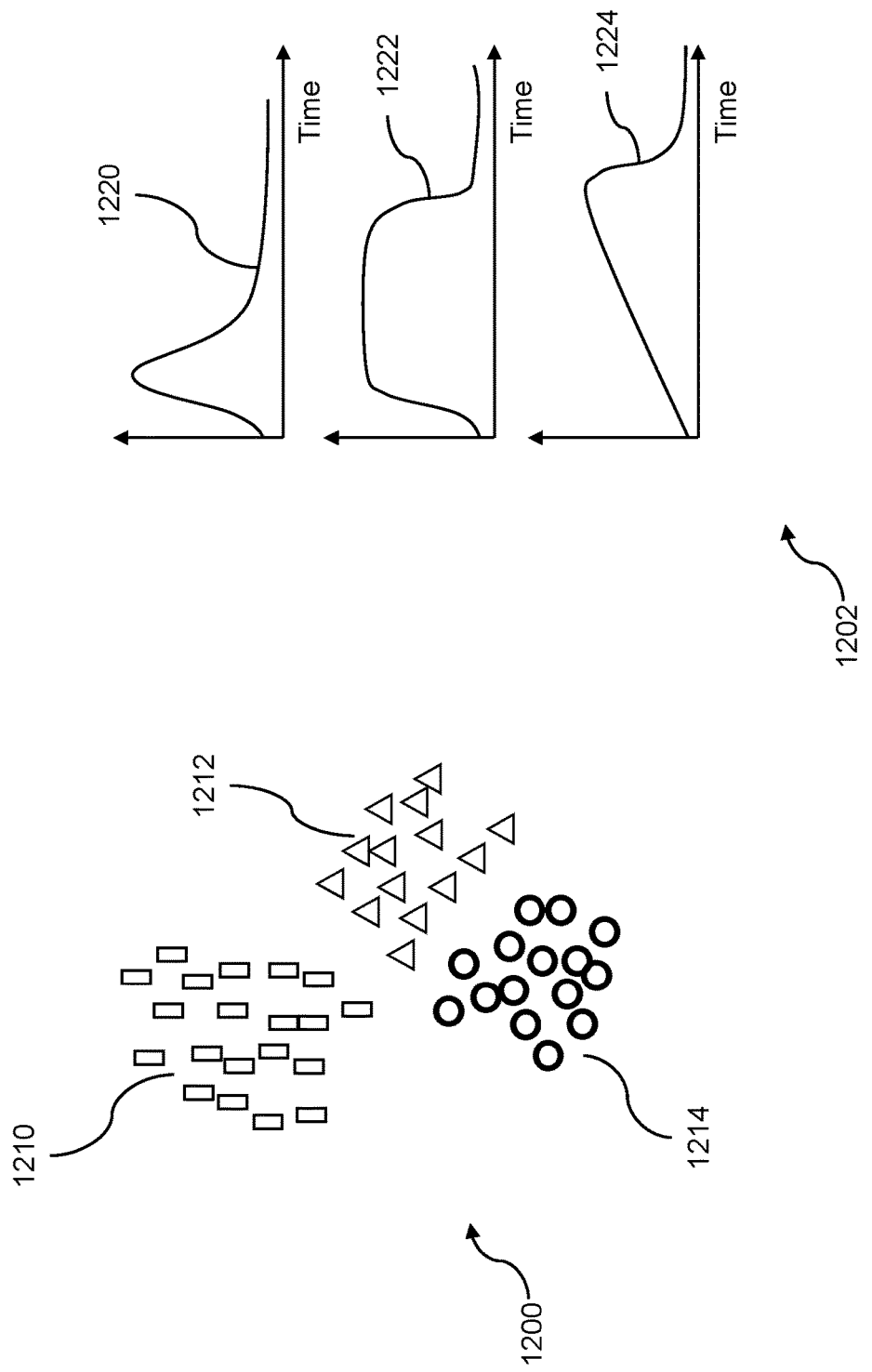
FIG. 12 shows unsupervised clustering of features and characterizations of cluster profiles.

FIG. 12 shows unsupervised clustering of features and characterizations of cluster profiles. Cognitive state vehicle navigation is based on image processing and modes. Vehicle occupant images are obtained, where the images include facial data. The images are analyzed to determine cognitive state data for the occupant. The cognitive state data is mapped to location data along a vehicle travel route, and the travel route information is updated based on the cognitive state data and mode data for the vehicle. The clustering of features and characterizations of cluster profiles can be performed for data collected from a remote computing device. The clustering of features and characterizations of cluster profiles can be performed for people as they interact with a vehicle. The sub-sectional components can be used with performing the evaluation of content of the face. The sub-sectional components can be used to provide a context. Features including samples of facial data can be clustered using unsupervised clustering. Various clusters, which include similar groupings of facial data observations, can be formed. The example 1200 shows three clusters, clusters 1210, 1212, and 1214. The clusters can be based on video collected from people who have opted-in to video collection. When the data collected is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1202 can be generated based on the clusters that can be formed from unsupervised clustering, with time shown on the x-axis and intensity or frequency shown on the y-axis. The cluster profiles can be based on captured facial data, including facial expressions. The cluster profile 1220 can be based on the cluster 1210, the cluster profile 1222 can be based on the cluster 1212, and the cluster profile 1224 can be based on the cluster 1214. The cluster profiles 1220, 1222, and 1224 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 13A:
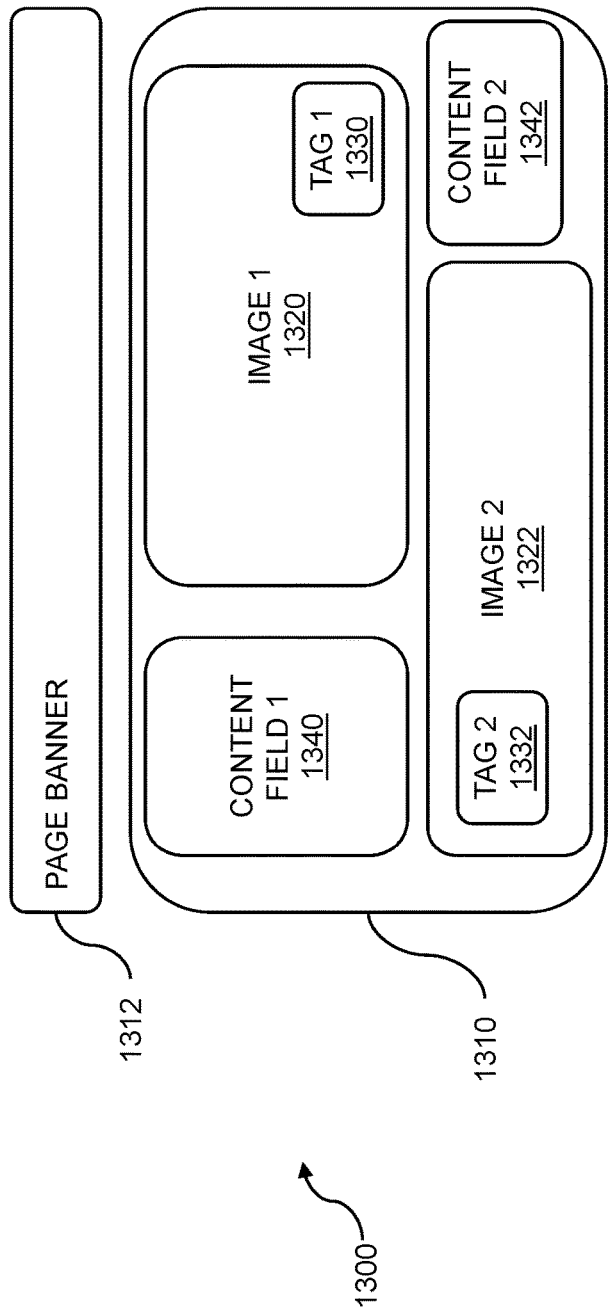
FIG. 13A shows example tags embedded in a webpage.

FIG. 13A shows example tags embedded in a webpage. Cognitive state vehicle navigation is based on image processing and modes. In some embodiments, screens within a vehicle can use embedded tags. Images of a vehicle occupant are obtained using a first imaging device within a vehicle. The one or more images include facial data of the vehicle occupant. The one or more images are analyzed to determine cognitive state data for the vehicle occupant. The cognitive state data is mapped to location data along a vehicle travel route, and information about the vehicle travel route is updated based on the cognitive state data and mode data for the vehicle. The tags embedded in the webpage can be used for image analysis for data collected from a remote computing device. The tags embedded in the webpage can be used by people as they interact with a vehicle. Once a tag is detected, a mobile device, a server, semiconductor-based logic, etc. can be used to evaluate associated facial expressions. A webpage 1300 can include a page body 1310, a page banner 1312, and so on. The page body can include one or more objects, where the objects can include text, images, videos, audio, and so on. The example page body 1310 shown includes a first image, image 1 1320; a second image, image 2 1322; a first content field, content field 1 1340; and a second content field, content field 2 1342. In practice, the page body 1310 can contain multiple images and content fields and can include one or more videos, one or more audio presentations, and so on. The page body can include embedded tags, such as tag 1 1330 and tag 2 1332. In the example shown, tag 1 1330 is embedded in image 1 1320, and tag 2 1332 is embedded in image 2 1322. In embodiments, multiple tags are embedded. Tags can also be embedded in content fields, in videos, in audio presentations, etc. When a user mouses over a tag or clicks on an object associated with a tag, the tag can be invoked. For example, when the user mouses over tag 1 1330, tag 1 1330 can then be invoked. Invoking tag 1 1330 can include enabling a camera coupled to a user's device and capturing one or more images of the user as the user views a media presentation (or digital experience). In a similar manner, when the user mouses over tag 2 1332, tag 2 1332 can be invoked. Invoking tag 2 1332 can also include enabling the camera and capturing images of the user. In other embodiments, other actions are taken based on invocation of the one or more tags. Invoking an embedded tag can initiate an analysis technique, post to social media, award the user a coupon or another prize, initiate cognitive state analysis, perform emotion analysis, and so on.

Figure 13B:
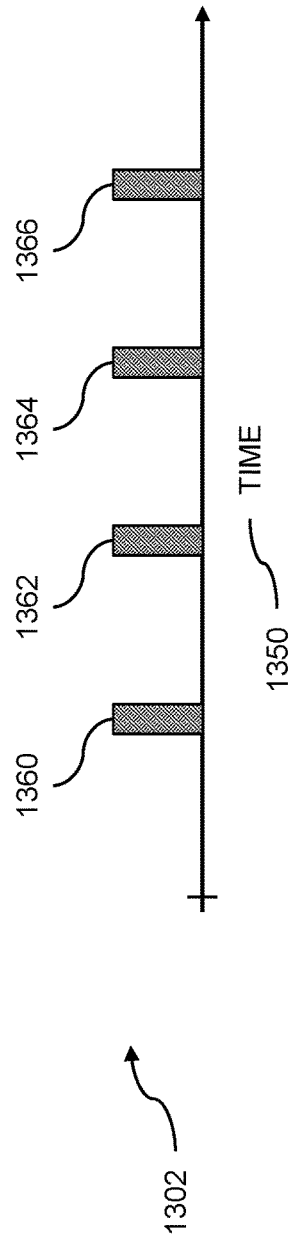
FIG. 13B shows invoking tags to collect images.

FIG. 13B shows invoking tags to collect images. Cognitive state vehicle navigation can be based on using image processing and modes. The image processing is based on obtaining images including facial data from a vehicle occupant. The images are analyzed to determine cognitive state data for the occupant, and the cognitive state data is mapped to location data along a vehicle travel route. The vehicle travel route is updated based on the cognitive state data and mode data for the vehicle. The invoking tags to collect images can be used for image analysis for data collected from a remote computing device. The invoking tags to collect images can be used for people as they interact with a vehicle. As previously stated, a media presentation can be a video, a webpage, and so on. A video 1302 can include one or more embedded tags, such as a tag 1360, a second tag 1362, a third tag 1364, a fourth tag 1366, and so on. In practice, multiple tags can be included in the media presentation. The one or more tags can be invoked during the media presentation. The collection of the invoked tags can occur over time, as represented by a timeline 1350. When a tag is encountered in the media presentation, the tag can be invoked. When the tag 1360 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has indicated an opt-out, then invoking the tag 1360 neither enables the camera nor captures images of the user during the media presentation. The user can indicate an opt-in for certain types of participation, where opting-in can be dependent on specific content in the media presentation. For example, the user could opt-in to participate in a study of political campaign messages and not opt-in for a particular advertisement study. In this case, tags that are related to political campaign messages, advertising messages, social media sharing, etc., and that enable the camera and image capture when invoked, would be embedded in the media presentation social media sharing, and so on. However, tags embedded in the media presentation that are related to advertisements would not enable the camera when invoked. Various other situations of tag invocation are also possible.

Figure 14:
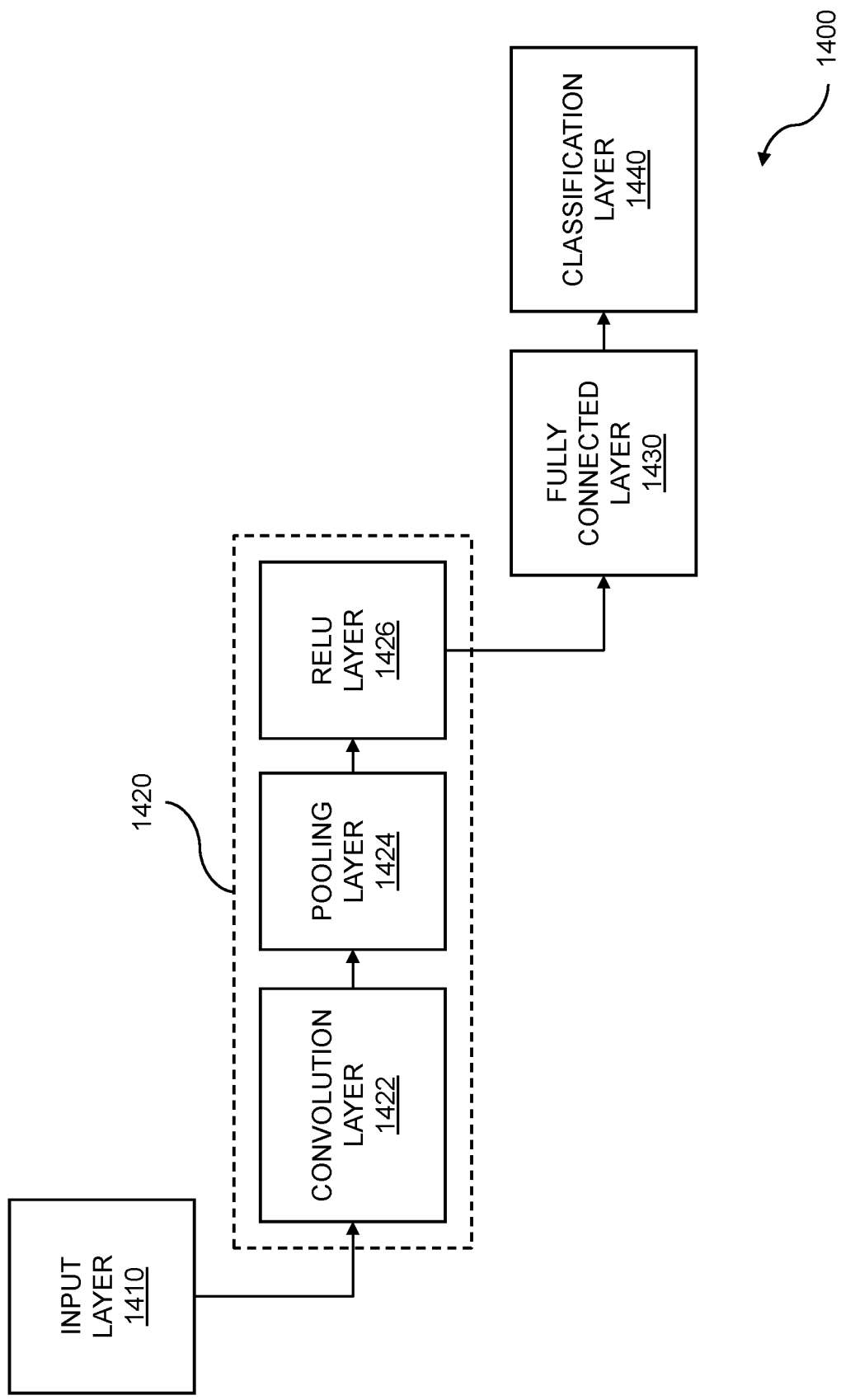
FIG. 14 is an example showing a convolutional neural network (CNN).

FIG. 14 is an example showing a convolutional neural network (CNN). A convolutional neural network such as 1400 can be used for deep learning, where the deep learning can be applied to cognitive state vehicle navigation based on image processing and modes. Images which include facial data are obtained from a vehicle occupant. The images are analyzed to determine cognitive state data for the vehicle occupant. The cognitive state data is mapped to location data along a vehicle travel route. Information about the vehicle travel route is updated based on the cognitive state data and modes for the vehicle, and the information that was updated is provided for vehicle control. The convolutional neural network can be applied to such tasks as cognitive state analysis, mental state analysis, mood analysis, emotional state analysis, and so on. Cognitive state data can include mental processes, where the mental processes can include attention, creativity, memory, perception, problem solving, thinking, use of language, or the like.

Cognitive analysis is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is important to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to the next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 14 is an example showing a convolutional neural network 1400. The convolutional neural network can be used for deep learning, where the deep learning can be applied to avatar image animation using translation vectors. The deep learning system can be accomplished using a convolution neural network or other techniques. The deep learning can accomplish facial recognition and analysis tasks. The network includes an input layer 1410. The input layer 1410 receives image data. The image data can be input in a variety of formats, such as JPEG, TIFF, BMP, and GIF. Compressed image formats can be decompressed into arrays of pixels, wherein each pixel can include an RGB tuple. The input layer 1410 can then perform processing such as identifying boundaries of the face, identifying landmarks of the face, extracting features of the face, and/or rotating a face within the plurality of images.

The network includes a collection of intermediate layers 1420. The multilayered analysis engine can include a convolutional neural network. Thus, the intermediate layers can include a convolution layer 1422. The convolution layer 1422 can include multiple sublayers, including hidden layers within it. The output of the convolution layer 1422 feeds into a pooling layer 1424. The pooling layer 1424 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 1424. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 1426. The output of the pooling layer 1424 can be input to the RELU layer 1426. In embodiments, the RELU layer implements an activation function such as $f(x)=\max(0,x)$, thus providing an activation with a threshold at zero. In some embodiments, the RELU layer 1426 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1422 and one or more hidden layers, and wherein the multilayered analysis engine can be used for emotional analysis.

The example 1400 includes a fully connected layer 1430. The fully connected layer 1430 processes each pixel/data point from the output of the collection of intermediate layers 1420. The fully connected layer 1430 takes all neurons in the previous layer and connects them to every single neuron it has. The output of the fully connected layer 1430 provides input to a classification layer 1440. The output of the classification layer 1440 provides a facial expression and/or cognitive state as its output. Thus, a multilayered analysis engine such as the one depicted in FIG. 14 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms.

Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include the person being more engaged, where engagement is based on affect, the person spending more time playing an online game or navigating a webpage, the person converting by buying a product or service, and so on. The reinforced learning can be based on exploring a solution space and adapting the model, algorithm, etc., based on outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 15:
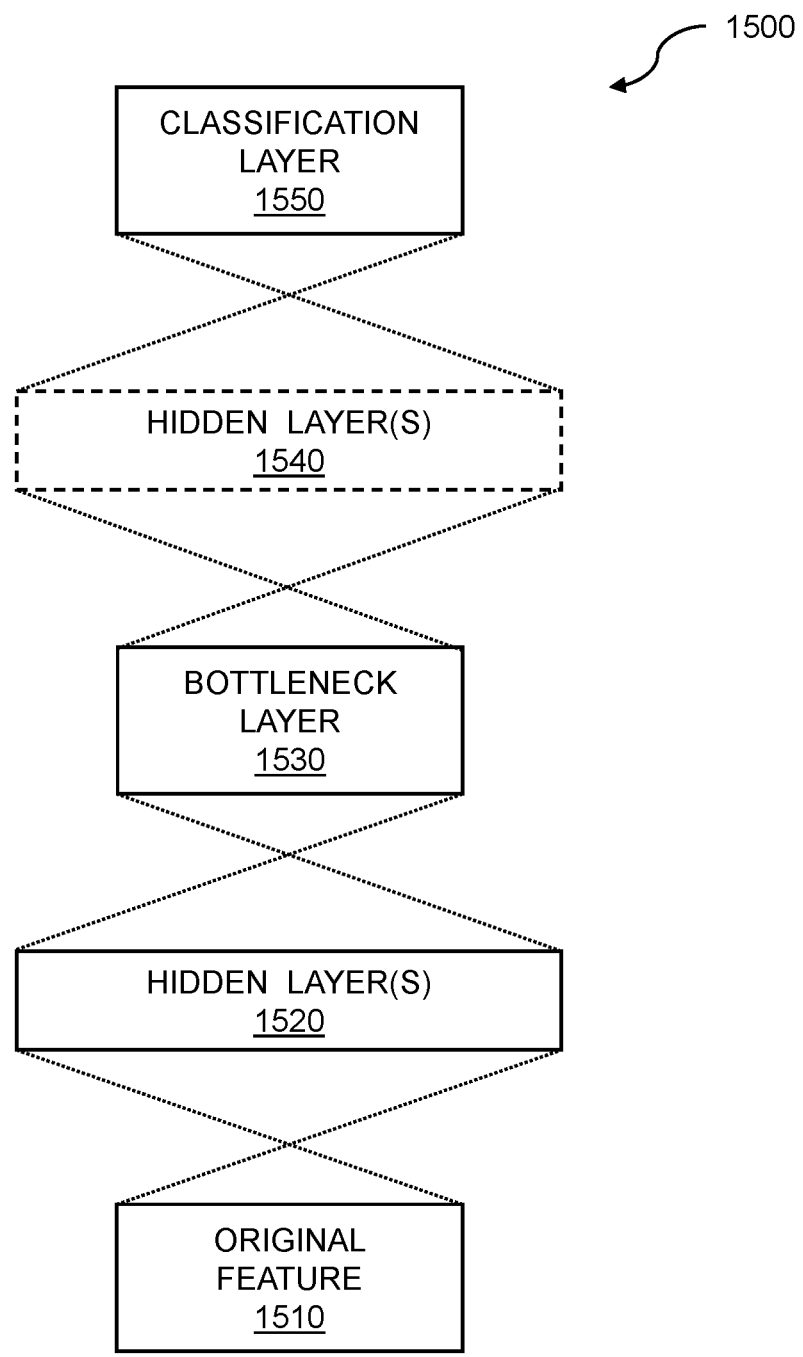
FIG. 15 illustrates a bottleneck layer within a deep learning environment.

FIG. 15 illustrates a bottleneck layer within a deep learning environment. A plurality of layers in a deep neural network (DNN) can include a bottleneck layer. The bottleneck layer can be used for cognitive state vehicle navigation based on image processing. A deep neural network can apply classifiers such as image classifiers, audio classifiers, and so on. The classifiers can be learned by analyzing cognitive state data. Images of a vehicle occupant are obtained, where the images include facial data. The images are analyzed to determine cognitive state data for the vehicle occupant. The cognitive state data is mapped to location data along a vehicle travel route, and the vehicle travel route is updated based on the cognitive state data and mode data for the vehicle.

Layers of a deep neural network can include a bottleneck layer 1500. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1510. A feature such as an image feature can include points, edges, objects, boundaries between and among regions, properties, and so on. The deep neural network can include one or more hidden layers 1520. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice.

In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1530. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include further hidden layers 1540. The number of the hidden layers can include zero hidden layers, one hidden layer, a plurality of hidden layers, and so on. The hidden layers following the bottleneck layer can include more nodes than the bottleneck layer. The deep neural network can include a classification layer 1550. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 16:
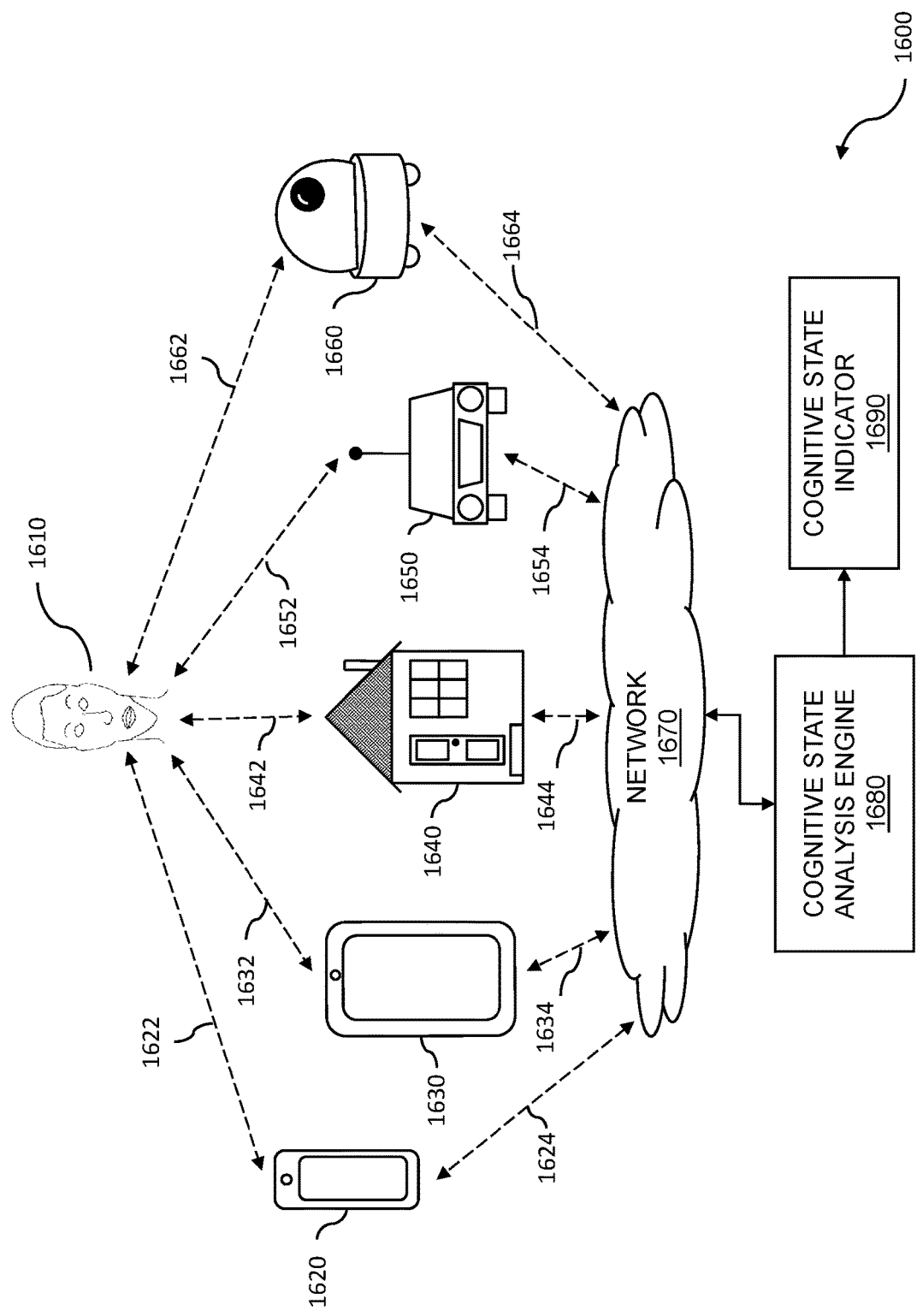
FIG. 16 shows data collection including devices and locations.

FIG. 16 shows data collection including devices and locations. Data, including video data and audio data, can be obtained for vehicle navigation based on image processing. The data can be obtained from multiple devices, vehicles, and locations. Cognitive state vehicle navigation is based on image processing and modes. One or more images of a vehicle occupant are obtained using a first imaging device within a vehicle. The one or more images can include facial data. A first computing device analyzes the one or more images to determine cognitive state data for the vehicle occupant. The cognitive state data is mapped to location data along a vehicle travel route. Information about the vehicle travel route is updated based on the cognitive state data and mode data for the vehicle. The information that was updated is provided for vehicle control.

In the data collection diagram 1600, multiple mobile devices, vehicles, and locations can be used separately or in combination to collect video data on a user 1610. The video data can include facial data. Other data such as audio data, physiological data, and so on, can be collected on the user. While one person is shown, the video data, or other data, can be collected on multiple people. A user 1610 can be observed as she or he is performing a task, experiencing an event, viewing a media presentation, and so on. The user 1610 can be shown one or more media presentations, political presentations, social media, or another form of displayed media. The one or more media presentations can be shown to a plurality of people. The media presentations can be displayed on an electronic display coupled to a client device. The data collected on the user 1610 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1610 can be analyzed and viewed for a variety of purposes including expression analysis, mental state analysis, cognitive state analysis, and so on. The electronic display can be on a smartphone 1620 as shown, a tablet computer 1630, a personal digital assistant, a television, a mobile monitor, or any other type of electronic device. In one embodiment, expression data is collected on a mobile device such as a cell phone 1620, a tablet computer 1630, a laptop computer, or a watch. Thus, the multiple sources can include at least one mobile device, such as a phone 1620 or a tablet 1630, or a wearable device such as a watch or glasses (not shown). A mobile device can include a front-facing camera and/or a rear-facing camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1610, data can be collected in a house 1640 using a web camera or the like; in a vehicle 1650 using a web camera, client device, etc.; by a social robot 1660, and so on.

As the user 1610 is monitored, the user 1610 might move due to the nature of the task, boredom, discomfort, distractions, or for another reason. As the user moves, the camera with a view of the user's face can be changed. Thus, as an example, if the user 1610 is looking in a first direction, the line of sight 1622 from the smartphone 1620 is able to observe the user's face, but if the user is looking in a second direction, the line of sight 1632 from the tablet 1630 is able to observe the user's face. Furthermore, in other embodiments, if the user is looking in a third direction, the line of sight 1642 from a camera in the house 1640 is able to observe the user's face, and if the user is looking in a fourth direction, the line of sight 1652 from the camera in the vehicle 1650 is able to observe the user's face. If the user is looking in a fifth direction, the line of sight 1662 from the social robot 1660 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1610 can also use a wearable device including a camera for gathering contextual information and/or collecting expression data on other users. Because the user 1610 can move her or his head, the facial data can be collected intermittently when she or he is looking in a direction of a camera. In some cases, multiple people can be included in the view from one or more cameras, and some embodiments include filtering out faces of one or more other people to determine whether the user 1610 is looking toward a camera. All or some of the expression data can be continuously or sporadically available from the various devices and other devices.

The captured video data can include cognitive content, such as facial expressions, etc., and can be transferred over a network 1670. The network can include the Internet or other computer network. The smartphone 1620 can share video using a link 1624, the tablet 1630 using a link 1634, the house 1640 using a link 1644, the vehicle 1650 using a link 1654, and the social robot 1660 using a link 1664. The links 1624, 1634, 1644, 1654, and 1664 can be wired, wireless, and hybrid links. The links can provide crowdsourced input for additional data, such as information on one or more travel routes. The crowdsourced travel route information can include travel route noise. The crowdsourced travel route information can include travel route construction information. The crowdsourced travel route information can include crowdsourced cognitive state data collected from other vehicle occupants traveling on the vehicle travel route. The crowdsourced travel route information can include travel route information on alternative travel routes or travel route segments.

The captured video data, including facial expressions, can be analyzed on a cognitive state analysis engine 1680, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 1690. The cognitive state indicator 1690 can indicate cognitive states, mental states, moods, emotions, etc. In embodiments, the cognitive content can include detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 17:
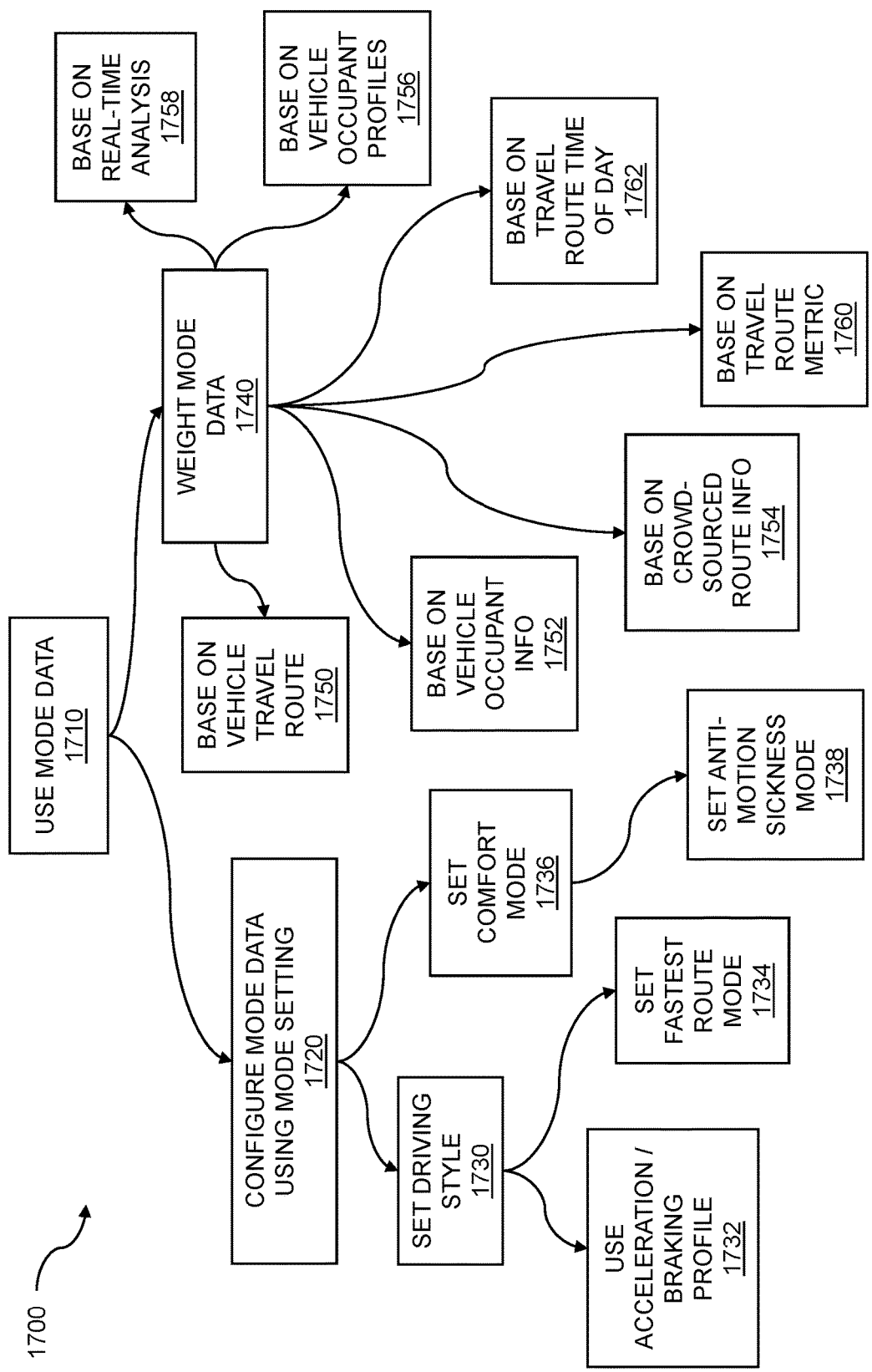
FIG. 17 is a flow diagram for using mode data.

FIG. 17 is a flow diagram of using mode data. Mode data can be used for vehicle navigation. Cognitive state vehicle navigation is based on image processing and modes. One or more images of a vehicle occupant are obtained using a first imaging device within a vehicle. The one or more images can include facial data. A first computing device analyzes the one or more images to determine cognitive state data for the vehicle occupant. The cognitive state data is mapped to location data along a vehicle travel route. Information about the vehicle travel route is updated based on the cognitive state data and mode data for the vehicle. The information that was updated is provided for vehicle control.

The flow 1700 includes using mode data 1710. The mode data 1710 can be for the vehicle rather than any one specific vehicle occupant, because the vehicle can only travel one route at one speed with one set of driving parameters, etc., at one time. The mode data can be configured using mode settings 1720. Mode settings can include an overall travel objective for the vehicle on a particular travel route, such as route selections, an approach to traversing a route, route change criteria, and so on. The mode settings can include a driving style, such as aggressive, cautious, average, etc. For example, if cognitive state data mapped to location data along a vehicle travel route indicates fear or uneasiness for one or more vehicle occupants, the information for a travel route can be updated to a slower, more gentle route if the mode settings indicate a cautious mode. Conversely, if the mode settings indicate an aggressive mode, a higher threshold for fear or uneasiness can be used before a travel route is updated. The mode setting can include setting a driving style 1730. The driving style can be fast, aggressive, gentle, slow, traffic-avoiding, and so on. The driving style can use an acceleration and/or braking profile 1732. The acceleration/braking profile can provide control information for the vehicle, such as hard accelerations and brakings for an aggressive profile, and so on. The driving style can include a fastest route driving style 1734, in which the most important factor in route selection and route traversal parameters are for the vehicle to get to its destination as quickly as legally possible. However, as will be discussed shortly, the mode data can be weighted to provide a balance for implementing a particular mode.

The mode setting can include a comfort mode 1736. The comfort mode can include a variety of parameters that influence route selection and route traversal parameters such as smooth roads, gentle acceleration and braking profiles, avoidance of windy roads, avoidance of stop-and-go traffic, and so on. Comfort mode can be geared to a number of vehicle occupant desires and needs, such as including setting an anti-motion sickness mode 1738. An anti-motion sickness mode can be used when an occupant easily becomes carsick, when an occupant is pregnant and experiencing morning sickness, when an occupant is inebriated and likely to become nauseous, and so on.

The use of mode data 1710 can include weighting the mode data 1740. Weighting mode data can provide a sophisticated process for including multiple mode inputs along with one or more occupants' cognitive states to influence the updating information. Various mode data weighting schemes can be used, such as basing the weighting on a vehicle travel route 1750, such as a selected or alternative route or route segment; on vehicle occupant information 1752, such as how many occupants, occupant ages, occupant identification, and so on; on crowdsourced route information 1754, such as travel route noise, travel route construction information, cognitive state data collected from other vehicle occupants traveling on a given vehicle travel route, etc.; on occupant cognitive state profiles 1756 obtained based on occupant identification; on occupant cognitive state information obtained using real-time analysis 1758 of the occupants using imaging or other cognitive state sensors; on a travel route metric 1760, such as an aggressiveness metric describing how aggressive other vehicles are performing on a given route; on a travel route time of day 1762, such as during the morning commute, during the evening commute, during the day or night, during off-peak travel hours, etc.; and so on.

Thus the mode data can be weighted based on profiles of one or more occupants of the vehicle. The mode data can be weighted based on real-time analysis of cognitive state data obtained for one or more occupants of the vehicle. The mode data can be weighted based on a travel route aggressiveness metric. The mode data can be weighted based on a time of day. Additionally, the cognitive state data can be weighted. The cognitive state data can be augmented by historical cognitive state data. Various embodiments of the flow 1700 can be included in a computer program product embodied in a non-transitory computer readable medium that includes code executable by one or more processors.

Figure 18:
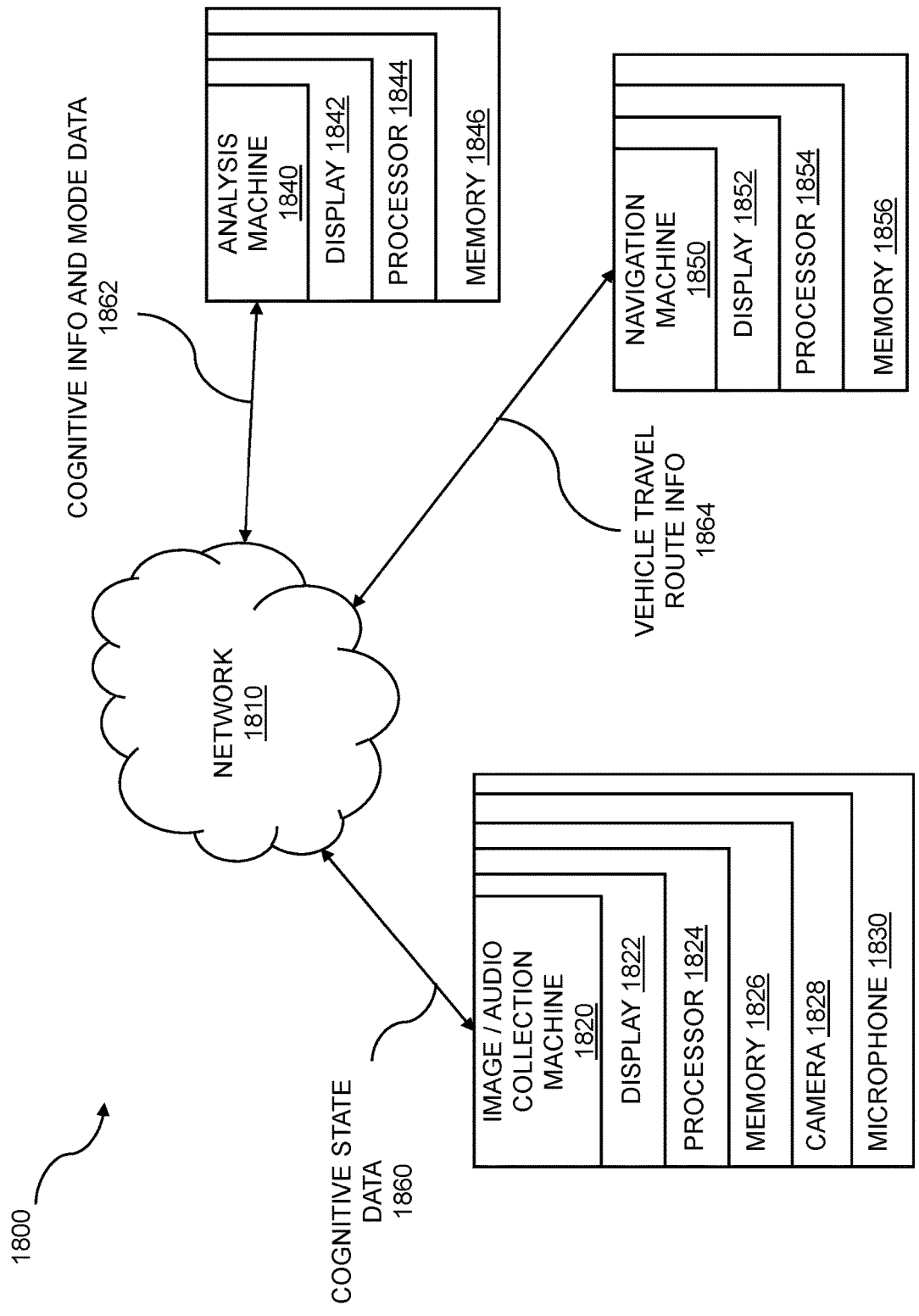
FIG. 18 is a diagram of a system for cognitive state vehicle navigation.

FIG. 18 is a diagram of a system 1800 for cognitive state vehicle navigation. Cognitive state vehicle navigation is based on image processing and modes. One or more images of a vehicle occupant are obtained using a first imaging device within a vehicle. The one or more images can include facial data. A first computing device analyzes the one or more images to determine cognitive state data for the vehicle occupant. The cognitive state data is mapped to location data along a vehicle travel route. Information about the vehicle travel route is updated based on the cognitive state data and mode data for the vehicle. The information that was updated is provided for vehicle control.

The network 1810, Internet, intranet, or another computer network, can be used for communication among various machines. An image and audio collection machine 1820 has a memory 1826 which stores instructions and one or more processors 1824 attached to the memory 1826, wherein the one or more processors 1824 can execute instructions. The image and audio collection machine 1820 can also have a network connection to carry cognitive state data 1860, and a display 1822 that can present cognitive state data, cognitive state profiles, mental state data, mental state profiles, emotional states, emotional state profiles, and so on. The image and audio collection machine 1820 can collect cognitive state data including image data, facial data, voice data, audio data, etc., from an occupant of a vehicle. In some embodiments, there are multiple image and audio collection machines 1820 that each collect cognitive state data including facial data. This type collection machine can have a camera 1828 and/or a microphone 1830. In many embodiments, both a camera and a microphone will be present. Further embodiments include obtaining audio information and augmenting the analyzing of the cognitive state data with the audio information. Once the cognitive state data 1860 has been collected, the image and audio collection machine 1820 can upload information to an analysis machine 1840, based on the cognitive state data from the occupant of the vehicle. The image and audio collection machine 1820 can communicate with the analysis machine 1840 over the network 1810, the Internet, some other computer network, or by another method suitable for communication between two machines. In some embodiments, the analysis machine 1840 functionality is embodied in the image and audio collection machine 1820.

The analysis machine 1840 can have a network connection for cognitive states or cognitive state information and mode data 1862, a memory 1846 which stores instructions, and one or more processors 1844 attached to the memory 1846, wherein the one or more processors 1844 can execute instructions. The analysis machine 1840 can receive cognitive state information, collected from an occupant of the vehicle, from the image and audio collection machine 1820, and can learn a cognitive state profile for the occupant. The analysis machine 1840 can also compare further cognitive state data with the cognitive state profile while the occupant is in a second vehicle. In some embodiments, the analysis machine 1840 also allows a user to view and evaluate the cognitive state data and cognitive state profiles for the occupant of the vehicle using one or more displays 1842. The analysis machine 1840 can then provide the cognitive state information and mode data 1862 to the navigation machine 1850. The cognitive state information and mode data 1862 can be provided using a cognitive state profile. In some embodiments, the image and audio collection machine 1820 can also function as the navigation machine 1850.

The navigation machine 1850 can have a memory 1856 which stores instructions, and one or more processors 1854 attached to the memory 1856, wherein the one or more processors 1854 can execute instructions. The navigation machine can use a computer network, the Internet, or another computer communication method, to request the cognitive state information 1862 from the analysis machine. The navigation machine 1850 can receive vehicle travel route information 1864, based on the cognitive state data 1860, from the occupant of the vehicle. The cognitive state information and vehicle travel route information for the occupant can be presented on a display 1852. In some embodiments, the navigation machine is set up to receive cognitive state data collected from an occupant of the vehicle, in a real-time or near real-time embodiment. In other embodiments, the navigation machine is set up to receive the cognitive state data on an intermittent basis. In at least one embodiment, a single computer incorporates the image and audio collection machine, the analysis machine, and the navigation machine functionalities.

Some embodiments comprise a computer system for vehicle navigation comprising: a memory which stores instructions; one or more processors coupled to the memory wherein the one or more processors, when executing the instructions which are stored, are configured to: obtain one or more images of a vehicle occupant using a first imaging device within a vehicle, wherein the one or more images include facial data of the vehicle occupant; analyze the one or more images to determine cognitive state data for the vehicle occupant; map the cognitive state data to location data along a vehicle travel route; update information about the vehicle travel route based on the cognitive state data mode data for the vehicle; and provide the information that was updated for vehicle control.

Some embodiments comprise a computer program product embodied in a non-transitory computer readable medium for vehicle navigation, the computer program product comprising code which causes one or more processors to perform operations of: obtaining one or more images of a vehicle occupant using a first imaging device within a vehicle, wherein the one or more images include facial data of the vehicle occupant; analyzing, using a first computing device, the one or more images to determine cognitive state data for the vehicle occupant; mapping the cognitive state data to location data along a vehicle travel route; updating information about the vehicle travel route based on the cognitive state data and mode data for the vehicle; and providing the information that was updated for vehicle control.

Each of the above methods may be executed on one or more processors on one or more computer systems. Embodiments may include various forms of distributed computing, client/server computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer-implemented method for vehicle navigation comprising:
   obtaining one or more images of a vehicle occupant using a first imaging device within a vehicle, wherein the one or more images include facial data of the vehicle occupant;
   analyzing, using a first computing device, the one or more images to determine cognitive state data for the vehicle occupant, wherein the analyzing uses a machine learning technique that utilizes a deep convolutional neural network;
   mapping the cognitive state data to location data along a vehicle travel route;
   weighting mode data based on real-time analysis of cognitive state data obtained for one or more occupants of the vehicle, wherein the weighting of the mode data is further based on travel route noise;
   updating information about the vehicle travel route based on the weighting of the mode data, wherein the weighting of the mode data is based on the travel route noise, the cognitive state data, and the mode data for the vehicle; and
   providing the information that was updated for vehicle control.

2. The method of claim 1 wherein the mode data is configurable based on a mode setting.

3. The method of claim 2 wherein the mode setting includes a driving style.

4. The method of claim 3 wherein the driving style includes a fastest route driving style.

5. The method of claim 3 wherein the driving style includes an acceleration and/or braking profile.

6. The method of claim 2 wherein the mode setting includes a comfort mode.

7. The method of claim 6 wherein the comfort mode includes an anti-motion sickness mode.

8. The method of claim 1 wherein the weighting the mode data is based on the vehicle travel route.

9. The method of claim 1 wherein the mode data is weighted based on information about one or more vehicle occupants.

10. The method of claim 1 wherein the mode data is weighted based on crowdsourced travel route information.

11. The method of claim 10 wherein the crowdsourced travel route information includes travel route noise.

12. The method of claim 10 wherein the crowdsourced travel route information includes travel route construction information.

13. The method of claim 10 wherein the crowdsourced travel route information includes crowdsourced cognitive state data collected from other vehicle occupants traveling on the vehicle travel route.

14. The method of claim 1 wherein the mode data is weighted based on profiles of one or more occupants of the vehicle.

15. The method of claim 1 wherein the mode data is weighted based on a travel route aggressiveness metric.

16. The method of claim 1 wherein the mode data is weighted based on a time of day.

17. The method of claim 1 further comprising weighting the cognitive state data.

18. The method of claim 17 wherein the cognitive state data is augmented by historical cognitive state data.

19. The method of claim 1 further comprising augmenting the cognitive state data with data obtained from one or more sensors that sense data from outside the vehicle.

20. The method of claim 19 wherein the data from outside the vehicle includes image data.

21. The method of claim 19 wherein the data from outside the vehicle includes radar data.

22. The method of claim 19 wherein the data from outside the vehicle includes one or more of outside temperature, time of day, level of daylight, weather conditions, traffic conditions, velocity of other vehicles, pedestrian mapping, or wireless governmental travel route advisories.

23. A computer program product embodied in a non-transitory computer readable medium for vehicle navigation, the computer program product comprising code which causes one or more processors to perform operations of:
   obtaining one or more images of a vehicle occupant using a first imaging device within a vehicle, wherein the one or more images include facial data of the vehicle occupant;
   analyzing, using a first computing device, the one or more images to determine cognitive state data for the vehicle occupant, wherein the analyzing uses a machine learning technique that utilizes a deep convolutional neural network;
mapping the cognitive state data to location data along a vehicle travel route;
weighting mode data based on real-time analysis of cognitive state data obtained for one or more occupants of the vehicle, wherein the weighting of the mode data is further based on travel route noise;
updating information about the vehicle travel route based on the weighting of the mode data, wherein the weighting of the mode data is based on the travel route noise, the cognitive state data, and the mode data for the vehicle; and
providing the information that was updated for vehicle control.

24. A computer system for vehicle navigation comprising:
a memory which stores instructions;
one or more processors coupled to the memory wherein the one or more processors, when executing the instructions which are stored, are configured to:
 obtain one or more images of a vehicle occupant using a first imaging device within a vehicle, wherein the one or more images include facial data of the vehicle occupant;
 analyze, using a machine learning technique that utilizes a deep convolutional neural network, the one or more images to determine cognitive state data for the vehicle occupant;
 map the cognitive state data to location data along a vehicle travel route;
 weight mode data based on real-time analysis of cognitive state data obtained for one or more occupants of the vehicle, wherein the weighting of the mode data is further based on travel route noise;
 update information about the vehicle travel route based on the mode data that was weighted based on the travel route noise, the cognitive state data, and the mode data for the vehicle; and
 provide the information that was updated for vehicle control.

25. The method of claim 9 wherein the information includes ages of the one or more occupants.

26. The method of claim 2 wherein the mode setting includes a cautious mode, and wherein the cautious mode causes selection of a slower travel route in response to cognitive state data for the vehicle occupant that indicates fear.

* * * * *